US006599718B1

(12) United States Patent
Liu et al.

(10) Patent No.: US 6,599,718 B1
(45) Date of Patent: Jul. 29, 2003

(54) GROWTH HORMONE SECRETAGOGUE RELATED RECEPTORS AND NUCLEIC ACIDS

(75) Inventors: Qingyun Liu, North Wales, PA (US); Andrew D. Howard, Park Ridge, NJ (US); Karen Kulju McKee, Middletown, NJ (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/743,742

(22) Filed: Mar. 15, 2001

Related U.S. Application Data

(60) Provisional application No. 60/092,623, filed on Jul. 13, 1998.

(51) Int. Cl.[7] ............... C12N 15/12; C12N 5/10; C12N 15/63; C07K 14/47
(52) U.S. Cl. ............ 435/69.1; 435/71.1; 435/471; 435/252.3; 435/325; 435/320.1; 536/23.5; 530/350
(58) Field of Search ............ 435/69.1, 71.1, 435/471, 252.3, 325, 320.1; 536/23.5; 530/350

(56) References Cited

U.S. PATENT DOCUMENTS

| | | | |
|---|---|---|---|
| 3,239,345 A | 3/1966 | Hodge et al. | 514/270 |
| 4,036,979 A | 7/1977 | Asato | 514/443 |
| 4,410,513 A | 10/1983 | Momany | 424/177 |
| 4,411,890 A | 10/1983 | Momany | 514/17 |
| 5,057,417 A | 10/1991 | Hammonds et al. | 435/69.1 |
| 5,206,235 A | 4/1993 | Fisher et al. | 514/210 |
| 5,283,241 A | 2/1994 | Bochis et al. | 514/183 |
| 5,284,841 A | 2/1994 | Chu et al. | 514/183 |
| 5,310,737 A | 5/1994 | Fisher et al. | 514/215 |
| 5,317,017 A | 5/1994 | Ok et al. | 514/211 |
| 5,374,721 A | 12/1994 | Schoen et al. | 540/491 |
| 5,430,144 A | 7/1995 | Schoen et al. | 540/461 |
| 5,434,261 A | 7/1995 | Schoen et al. | 540/461 |
| 5,438,136 A | 8/1995 | Devita et al. | 540/456 |
| 5,492,916 A | 2/1996 | Morriello et al. | 514/318 |
| 5,492,920 A | 2/1996 | Chen et al. | 514/323 |
| 5,494,919 A | 2/1996 | Morriello et al. | 514/323 |
| 5,583,010 A | 12/1996 | Baumbach et al. | 435/69.1 |
| 5,591,641 A | 1/1997 | Thorner et al. | 435/69.1 |
| 5,830,433 A | 11/1998 | Dean et al. | 424/181 |

FOREIGN PATENT DOCUMENTS

| | | |
|---|---|---|
| EP | 0 144 230 | 3/1984 |
| EP | 0 513 974 | 12/1992 |
| WO | WO 89/07110 | 8/1989 |
| WO | WO 89/07111 | 8/1989 |
| WO | WO 93/04081 | 3/1993 |
| WO | WO 94/07486 | 4/1994 |
| WO | WO 94/08583 | 4/1994 |
| WO | WO 94/11012 | 5/1994 |
| WO | WO 94/13696 | 6/1994 |
| WO | WO 94/19367 | 9/1994 |
| WO | WO 95/03289 | 2/1995 |
| WO | WO 95/03290 | 2/1995 |
| WO | WO 95/09633 | 4/1995 |
| WO | WO 95/11029 | 4/1995 |
| WO | WO 95/12598 | 5/1995 |
| WO | WO 95/13069 | 5/1995 |
| WO | WO 95/14666 | 6/1995 |
| WO | WO 95/16675 | 6/1995 |
| WO | WO 95/16692 | 6/1995 |
| WO | WO 95/17422 | 6/1995 |
| WO | WO 95/17423 | 6/1995 |
| WO | WO 95/34311 | 12/1995 |
| WO | WO 96/02530 | 2/1996 |
| WO | WO 97/22004 | 6/1997 |
| WO | WO 98/14780 | 4/1998 |

OTHER PUBLICATIONS

Database GenBank (GenEmbl); Accession No.: AF044602; Mckee et al. Mus musclus orphan G protein Coupled receptor mRNA. Feb. 1998.*

Database GenBank (EST) Accession No.: AA562357; Marra et al; v126f01.rl stratagene mouse Tcell mRNA; Aug. 1997.*

Kozak, M. et al. "Compilation and analysis of sequences upstream from the translational start site in eukaryotic mRNAs", Nucleic Acids Research, 1984, vol. 12, pp. 857–872.

Button, D. et al. "Aequorin–expressing mammalian cell lines used to report Ca2+ mobilization", Cell Calcium, 1993, vol. 14, pp. 663–671.

Kao, J. et al. "Photochemically Generated Cytosolic Calcium Pulses and Their Detection by Fluo–3", The Journal of Biological Chemistry, 1989, vol. 264, pp. 8179–8184.

Zlokarnik, G. et al. "Quantitation of Transcription and Clonal Selection of Single Living Cells with beta–Lactamase as Reporter", Science, 1998, vol. 279, pp. 84–88.

Ok, D. et al. "Structure–Activity Relationships of the Non–Peptidyl Growth Hormone Secretagogue L–692–429", Bioorganic & Medicinal Chemistry Letters, 1994, vol. 4, pp. 2709–2714.

Patchett, A. et al. "Design and biological activities of L–163,191 (MK–0677): A potent, orally active growth hormone secretagogue", Proc. Natl. Acad. Sci. USA, 1995, vol. 92, pp. 7001–7005.

Schoen, W. et al. "Growth Hormone Secretagogues", Annual Reports in Medicinal Chemistry, 1993, vol. 28, pp. 177–186.

(List continued on next page.)

Primary Examiner—Prema Mertz
Assistant Examiner—Fozja Hamud
(74) Attorney, Agent, or Firm—Patricia Chisholm; Anna L. Cocuzzo; Jack L. Tribble

(57) ABSTRACT

This invention relates to a new family of receptors, growth hormone secretagogue-related receptors, which exhibit moderate sequence identity to both the growth hormone secretagogue receptor (GHS-R) and the neurotensin receptor (NT-R). These newly identified receptors are expressed in a diverse set of tissues. This invention also relates to nucleic acids encoding these receptors, and to the use of these receptors to identify ligands that modulate growth hormone release as well as other modulators of endocrine function.

6 Claims, 17 Drawing Sheets

OTHER PUBLICATIONS

Smith, R. et al. "A Nonpeptidyl Growth Hormone Secretagogue", Science, 1993, vol. 260, pp. 1640–1643.

King, K. et al. "Control of Yeast Mating Signal Transduction by a Mammalian B2–Adrenergic Receptor and Gs a Subunit", Science, 1990, vol. 250, pp. 121–123.

Julius, D. et al. "Molecular Characterization of a Functional cDNA Encoding the Serotonin 1c Receptor", Science, 1988, vol. 241, pp. 558–564.

Cubitt, A. et al. "Understanding, improving and using green fluorescent proteins", TIBS, 1995, vol. 20, pp. 448–455.

Feighner, S. et al. "Structural Requirements for the Activation of the Human Growth Hormone Secretagogue Receptor by Peptide and Nonpeptide Secretagogues", Molecular Endocrinology, 1998, vol. 12, pp. 137–145.

Williams, R. "Textbook of Endocrinology, Fifth Edition" 1974, pp. 790–791.

Wu, D. et al. "Activation of Phospholipase C by a1–Adrenergic Receptors Is Mediated by the a Subunits of Gq Family", The Journal of Biological Chemistry, 1992, vol. 267, pp. 25798–25802.

Ganong, W. "Review of Medical Physiology, seventeenth edition", pp. 373–374.

Cheng, K. et al. "Evidence for a Role of Protein Kinase–C in His–D–Trp–Ala–Trp–D–Phe–Lys–NH2–Induced Growth Hormone Release from Rat Primary Pituitary Cells", Endocrinology, 1991, vol. 129, pp. 3337–3342.

McKee, K. et al. "Molecular Analysis of Rat Pituitary and Hypothalamic Growth Hormone Secretagogue Receptors", Molecular Endocrinology, 1997, vol. 11, pp. 415–423.

Bennett, P. et al. "Hypothalamic Growth Hormone Secretagogue–Receptor (GHS–R) Expression Is Regulated by Growth Hormone in the Rat", Endocrinology, 1997, vol. 138, pp. 4552–4557.

Minamino, N. et al. "Neuromedin U–8 and U–25: Novel Uterus Stimulating and Hypertensive Peptides Identified in Porcine Spinal Cord", Biochemical and Biophysical Research Communications, 1985, vol. 130, pp. 1078–1085.

Domin, J. et al. "Characterization of neuromedin U like immunoreactivity in rat, porcine, guinea–pig and human tissue extracts using a specific radioimmunoassay", Biochem. Biophys. Res. Commun., 1986, vol. 140, pp. 1127–1134.

Conlon, J. et al. "Primary Structure of Neuromedine U from the Rat", Journal of Neurochemistry, 1988, vol. 51, pp. 988–991.

Minamino, N. et al. "Isolation and Structural Determination of Rat Neuromedin U", Biochemical Biophysical Research Communications, 1988, vol. 156, pp. 355–360.

Domin, J. et al. "The Distribution, Purification, and Pharmacological Action of an Amphibian Neuromedin U", The Journal of Biological Chemistry, 1989, vol. 264, pp. 20881–20885.

O'Harte, F. et al. "Isolation, Structure Characterization and Pharmacological Activity of Dog Neuromedin U", Peptides, 1991, vol. 12, pp. 11–15.

Kage, R. et al. "Rabbit neuromedin U–25: lack of conservation of a posttranslation processing site", Regulatory Peptides, 1991, vol. 33, pp. 191–198.

Domin, J. et al. "The purification and sequence analysis of an avian neuromedin U", Regulatory Peptides, 1992, vol. 41, pp. 1–8.

Lo, G. et al. "Characterization of Complementary DNA Encoding the Rat Neuromedin U Precursor", Molecular Endocrinology, 1992, vol. 6, pp. 1538–1544.

Austin, C. et al. "Cloning and characterization of the cDNA encoding the human neuromedin U (NmU) precursor: NmU expression in the human gastrointestinal tract", Journal of Molecular Endocrinology, 1995, vol. 14, pp. 157–169.

Nandha, K. et al. "Characterization of the Rat Uterine Neuromedin U Receptor", Endocrinology, 1993, vol. 133, pp. 482–486.

Soldati, T. et al. "Alternative Ribosomal Initiation Gives Rise to Chicken Brain–type Creatine Kinase Isoproteins with Heterogeneous Amino Termini", The Journal of Biological Chemistry, 1990, vol. 265, pp. 4498–4506.

Howard, A. et al. "A Receptor in Pituitary and Hypothalamus That Functions in Growth Hormone Release", Science, 1996, vol. 273, pp. 974–977.

Aloi, J. et al. "Neuroendocrine Responses to a Novel Growth Hormone Secretagogue, L–692,429, in Healthy Older Subjects", Journal of Clinical Endocrinology and Metabolism, 1994, vol. 79, pp. 943–949.

Bowers, C. "Editorial: On a Peptidomimetic Growth Hormone–Releasing Peptide", Journal of Clinical Endocrinology and Metabolism, 1994, vol. 79, pp. 940–942.

Sethumadhavan, K. et al. "Demonstration and Characterization of the Specific Binding of Growth Hormone–Releasing Peptide to Rat Anterior Pituitary and Hypothalamic Membranes", Biochemical and Biophysical Research Communications, 1991, vol. 178, pp. 31–37.

Pomes, A. et al. "Solubilization and Characterization of a Growth Hormone Secretagogue Receptor from Porcine Anterior Pituitary Membranes", Biochemical and Biophysical Research Communications, 1996, vol. 225, pp. 939–945.

Guan, X. et al. "Distribution of mRNA encoding the growth hormone secretagogue receptor in brain and peripheral tissues", Molecular Brain Research, 1997, vol. 48, pp. 23–29.

Pong, S. et al. "Identification of A New G–Protein–Linked Receptor for Growth Hormone Secretagogues", Molecular Endocrinology, 1996, vol. 10, pp. 57–61.

McKee, K. et al., Database Genbank, Accession No. 055040, 1998.

Tan, C. et al., Database Genbank, Accession No. 043664, 1998.

McKee, K. et al., Database Genbank, Accession No. AF044602, 1998.

Tan, C. et al., Database Genbank, Accession No. AF044600, 1999.

Adams, E. et al. "Presence of Growth Hormone Secretagogue Receptor Messenger Ribonucleic Acid in Human Pituitary Tumors and Rat GH3 Cells", Journal of Clinical Endocrinology and Metabolism, 1998, vol. 83, pp. 638–642.

Howard, A. et al. "Molecular Analysis of the Growth Hormone Secretagogue Receptor", Growth Hormone Secretagogues, 1999, pp. 35–51.

McKee, K. et al. "Cloning and Characterization of Two Human G Protein–Coupled Receptor Genes (GPR38 and GPR39) Related to the Growth Hormone Secretagogue and Neurotensin Receptors", Genomics, 1997, vol. 46, pp. 426–434.

Feighner, S. et al. "Receptor for Motilin Identified in the Human Gastrointestinal System", Science, 1999, vol. 284, pp. 2184–2188.

* cited by examiner

```
-308  ACCTGCCTGCCTCAGCTTCCTTCGCTTGGGATTAAAGCTCCCCACTACCACTGCCCCGGCCAATTTTATTATTTCAAGG      -229
-228  TTTGACTCCGAATACTCTGTAGTGAAATGCACTTTAGTGCGTGGCAGATGCTTTCTTTCCAGTGGCATGTGACTAAT      -149
-148  CAGTCCTCTACAGTGTGCCTGTGATAACTTAGGACAGAGCTGGGATTACCTAACTAAATGACTTCTCGGTATCTCCCCCTCTATCCTAC   -69
-68   AGACTCCTCCCTGCCTCAATGTCCATCTTTCCTGGAGCGCTCTCCCAAATGTCTCCCAAATGTTCAAGGAGCCCC      -1

+1    ATG GTC TGC AAT ATC AGT GAG TTC AAG TGG CCC TAT CAA CCT GAG GAT CTG AAC CTT ACC     60
1     M   V   C   N   I   S   E   F   K   W   P   Y   Q   P   E   D   L   N   L   T      20
                                                                            TM-1

61    GAT GAG GCC CTG AGG CTG AAG TAT TTG GGC CCA CAG CAG CAG ATG AAA CAG TTT GTC CCC ATC  120
21    D   E   A   L   R   L   K   Y   L   G   P   Q   Q   Q   M   K   Q   F   V   P   I   40

121   TGT GTC ACG TAC CTG CTC ATC TTC GTG GTC GGC ACT CTG GGC AAC GGG CTG ACC TGC ACC     180
41    C   V   T   Y   L   L   I   F   V   V   G   T   L   G   N   G   L   T   C   T      60
                                                                    TM-2

181   GTG ATC CTG CGC AAC AAG ACT ATG CGC CTG CTG GTG GGC TTG CCT CTT GAG CTT TAT GAG ACC  240
61    V   I   L   R   N   K   T   M   R   L   L   V   G   L   P   L   E   L   Y   E   T   80
                                                            TM-3

241   GTG TCC GAT ATG CTG GTC CTA CTC GTG CTG GGT GCC AGT GCC TGC TAC TTC CGA ATA CTC CTC TTA GAG ACC  300
81    V   S   D   M   L   V   L   L   V   L   G   A   S   A   C   Y   F   R   I   L   L   L   E   T  100

301   AAT TAC CCG TTC CAG CTC CAA CTG GGA GCC AGT GCC TGT GTC ACA GCC CTG AGT GTG GAG CGT TAT GTC GCC GTG  360
101   N   Y   P   F   Q   L   Q   L   G   A   S   A   C   V   T   A   L   S   V   E   R   Y   V   A   V  120

361   GTC TGC CTA GCT TCA GTG CTC AAT GTC AAC ACA GCC CAT GTC GCC CGC ATG GGG  420
121   V   C   L   A   S   V   L   N   V   N   T   A   L   S   V   E   R   Y   V   A   V  140
                                                                    TM-4

421   GTG CGG CCC CTA CAA CTC CAA GCC CAA AAG TCT GTG ATG ACA CGG GCC CAT GTC CGC CGC ATG GTG GGG  480
141   V   R   P   L   Q   A   Q   K   S   V   M   T   R   A   H   V   R   R   M   V   G  160
```

```
1021 TTC CGA GAG ACC TTC CTG CAA GCC CTG GGC CTT GGA ACC CAG TGC TGT CAT CGC CGC CAA  1080
 341  F   R   E   T   F   L   Q   A   L   G   L   G   T   Q   C   C   H   R   R   Q    360

1081 CCC TAT CAT GGC TCC CAT AAC CAC ATC AGG TTG ACC ACA GGC AGC ACC CTG TGT GAC GTG  1140
 361  P   Y   H   G   S   H   N   H   I   R   L   T   T   G   S   T   L   C   D   V    380

1141 GGC CAC AGG AAC AGC AGG GAC GAA CCT CTG GCT GTG AAT GAG GAT CCA GGG TGT CAG CAA  1200
 381  G   H   R   N   S   R   D   E   P   L   A   V   N   E   D   P   G   C   Q   Q    400

1201 GAG ACA GAC CCC TCC TGA                                                            1218
 401  E   T   D   P   S   *                                                              406
```

FIG. 1C

```
  1 ATG GCT TGC AAT GGC AGT GCC GCC AGG GGG CAC TTT GAC CCT GAG GAC TTG AAC CTG ACT    60
  1  M   A   C   N   G   S   A   A   R   G   H   F   D   P   E   D   L   N   L   T    20

61 GAC GAG GCA CTG AGA CTC AAG TAC CTG GGG CCC CAG ACA GAG CTG TTC ATG CCC ATC         120
 21  D   E   A   L   R   L   K   Y   L   G   P   Q   T   E   L   F   M   P   I         40
                                                    TM-1
121 TGT GCC ACA TAC CTG CTG ATC TTC GTG GTG GCT GTG GGC AAT GGG CTG ACC TGT CTG        180
 41  C   A   T   Y   L   L   I   F   V   V   G   A   V   G   N   G   L   T   C   L     60
                TM-2
181 GTC ATC CTG CCC CAC AAG GCC ATG CGC ACG CCT ACC AAC TAC TAC CTC TTC AGC CTG GCC    240
 61  V   I   L   R   H   K   A   M   R   T   P   T   N   Y   Y   L   F   S   L   A     80

241 GTG TCG GAC CTG CTG GTG CTG CTG GTG GGC CTG CCC CTG GAG CTC TAT GAG ATG TGG CAC    300
 81  V   S   D   L   L   V   L   L   V   G   L   P   L   E   L   Y   E   M   W   H    100
                                        TM-3
301 AAC TAC CCC TTC CTG CTG GGC GTT GGT GGC TGC TAT TTC CGC ACG CTA CTG TTT GAG ATG    360
101  N   Y   P   F   L   L   G   V   G   G   C   Y   F   R   T   L   L   F   E   M    120

361 GTC TGC CTG GCC TCA GTG CTC AAC GTC ACT GCC CTG AGC GTG GAA CGG TAT GTG GCC GTG    420
121  V   C   L   A   S   V   L   N   V   T   A   L   S   V   E   R   Y   V   A   V    140
                                                          TM-4
421 GTG CAC CCA CTG CAG GCC AGG TCC ATG ATG ACG CGG GCC CAT GTG CGC CGA GTG CTT GGG    480
141  V   H   P   L   Q   A   R   S   M   V   T   R   A   H   V   R   R   V   L   G    160

481 GCC GTC TGG GGT CTT GCC ATG CTC TGC TCC CTG CCC AAC ACC AGC CTG CCC AAC ATC CGG    540
161  A   V   W   G   L   A   M   L   C   S   L   P   N   T   S   L   P   N   I   R    180
```

FIG. 2A

```
541  CAG CTG CAC GTG CCC TGC CGG GGC CCA GTG CCA GAC TCA GCT GTT TGC ATG CTG GTC CCC   600
181   Q   L   H   V   P   C   R   G   P   V   P   D   S   A   V   C   M   L   V   R   200
                          TM-5
601  CCA CGG GCC CTC TAC AAC ATG GTA GTG CAG ACC ACC GCG CTG CTC TTG TTC TGC CTG CCC   660
201   P   R   A   L   Y   N   M   V   V   Q   T   T   A   L   L   F   C   L   P   220

661  ATG GCC ATC ATG AGC GTG CTC TAC CTG CTC ATT GGG CTG CGA CGG CGG GAG AGG CTG       720
221   M   A   I   M   S   V   L   Y   L   L   I   G   L   R   R   R   E   R   L       240

721  CTG CTC ATG CAG GAG GCC AAG GGC AGG GCC TCT GCA GCA GCC AGG TCC AGA TAC ACC TGC   780
241   L   L   M   Q   E   A   K   G   R   A   S   A   A   A   R   S   R   Y   T   C   260
                                                                      TM-6
781  AGG CTC CAG CAG CAC GAT CGG GGC CGG AGA CAA CGA GTG ACC AAG ATG CTG TTT GTC CTG GTC   840
261   R   L   Q   Q   H   D   R   G   R   R   Q   V   T   K   M   L   F   V   L   V   280

841  GTG GTG TTT GGC ATC TGC TGG GCC CCG TTC CAC GCC GAC CGC GTC ATG TGG AGC CTC GTG   900
281   V   V   F   G   I   C   W   A   P   F   H   A   D   R   V   M   W   S   V   V   300
                                                                              TM-7
901  TCA CAG TGG ACA GAT GGC CTG CAC CTG GCC TTC CAG CAC GTG CAC GTC ATC TCC GGC ATC   960
301   S   Q   W   T   D   G   L   H   L   A   F   Q   H   V   H   V   I   S   G   I   320

961  TTC TTC TAC CTG GGC TCG GCC GCC AAC CCC GTG CTC TAT AGC CTC ATG TCC AGC CGC TTC   1020
321   F   F   Y   L   G   S   A   A   N   P   V   L   Y   S   L   M   S   S   R   F   340

1021 CGA GAG ACC TTC CAG GAG GCC CTG TGC CTC GGG GCC TGC TGC CAT CGC CTC AGA CCC CGC   1080
341   R   E   T   F   Q   E   A   L   C   L   G   A   C   C   H   R   L   R   P   R   360
```

FIG. 2B

```
1081 CAC AGC TCC CAC AGC CTC AGC AGG ATG ACC ACA GGC AGC ACC CTG TGT GAT GTG GGC TCC 1140
 361  H   S   S   H   S   L   S   R   M   T   T   G   S   T   L   C   D   V   G   S   380

1141 CTG GGC AGC TGG GTC CAC CCC CTG GCT GGG AAC GAT GGC CCA GAG GCG CAG CAA GAG ACC 1200
 381  L   G   S   W   V   H   P   L   A   G   N   D   G   P   E   A   Q   Q   E   T   400

1201 GAT CCA TCC TGA                                                                  1212
 401  D   P   S   *                                                                   404
```

FIG. 2C

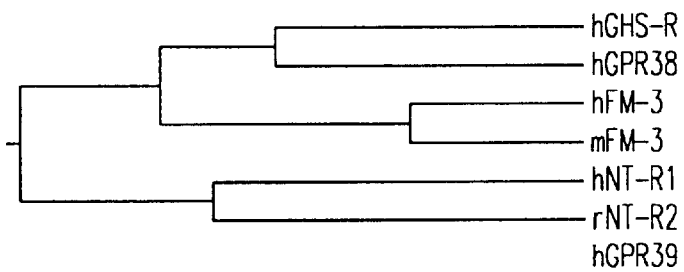

```
hNT-R1    1  MRLNSSAPGTPGTPAADPFQRAQAGLEEALLAPGFGNASGNASERVLAAPSSELDV  56
rNT-R2    1  M-ETSSPWPPRPSPSAGLSLE---------------------------ARLG      25
hGHS-R    1  M----WNATPSEEPGFNLTLADLD-WDASPGNDS----------LGDELLQLFP    39
hGPR38    1  M--GSPWNGSDGPEGAREPPWPALPPWDERRCSP---------------FP        34
hGPR39    1  M----ASPSLPGSDCSQIIDHSHV--------PEFEVAT-----------         27
hFM-3     1  M--AC---NGSAARGHFDP? EDLNLTDEALRLKY----------LGPQQTELF-   37
mFM-3     1  M--VC---NISEFKWPYQP ?EDLNLTDEALRLKY----------LGPQQMKQF-   37 hNT-R1    57 NTDIYSKVLVTAVYLALFVVGTVGNTVTAFTLARKKSLQSLQSTVHYHLGSLALSD  112
rNT-R2    26 VDTRLWAKVLFTALYSLIFAFGTAGNALSVHVVLKARA--GRPGRLRYHVLSLALS   79
hGHS-R    40 APLL---AGVTATCVALFVVGIAGNLLTMLVVSRFRE---LRTTTNLYLSSMAFSD   89
hGPR38    35 LGAV---VPVTAVCLCLFVVGVSGNMVTVMLIGRYRD---MRTTTNLYLGSMAVSD   84
hGPR39    28 ----WIKITLILVYLIIFVMGLLGNSATIRVTQVLQKKGYLQKEVTDHMVSLACSD   79
hFM-3     38 ------MPICATYLLIFVVGAVGNGLTCLVILRHKA---MRTPTNYYLFSLAVSD   83
mFM-3     38 ------VPICVTYLLIFVVGTLGNGLTCTVILRNKT---MRTPTNFYLFSLAVSD   83 hNT-R1   113 LLTLLLAMPVELYNFIWVHHPWAFGDAGCRGYYFLRDACTYATALNVASLSVERYL  168
rNT-R2    80 ALLLLLVSMPMELYNFVWSHYPWVFGDLGCRGYYFVRELCAYATVLSVASLSAERC  135
hGHS-R    90 LLIFL-CMPLDLVRL-WQYRPWNFGDLLCKLFQFVSESCTYATMLTITALSVERYF  143
hGPR38    85 LLILL-GLPFDLYRL-WRSRPWMFGPLLCRLSLYVGEGCTYATLLHMTALSVERYL  138
hGPR39    80 ILVFLIGMPMEFYSIIWNPLTTSSYTLSCKLHTFLFEACSYATLLHVLTLSFERYI  135
hFM-3     84 LLMLLVGLPLELYEM-WHNYPFLLGVGGCYFRTLLFEMVCLASVLNVITALSVERYV  138
mFM-3     84 MLVLLVGLPLELYEM-QQNYPFQLGASACYFRILLLETVCLASVLNVITALSVERYV  138 hNT-R1   169 AICHPFKAKTLMSRSRTKKFISAIWLASALLTVPMLFTMGEQNR----SADGQ-HA  219
rNT-R2   136 LAVCQPLRARRLLTPRRTRRLLSLVWVASLGLALPMAVIMGQKHE--VESADGEPE  189
hGHS-R   144 AICFPLRAKVVVTKGRVKLVIFVIWAVAFCSAGPIFVLVGVEHEHGTDP-------  192
hGPR38   139 AICRPLRARVLVTRRRVRALIAVLWAVALLSAGPFLFLVGVEQDPGISVVPGLNGT  194
hGPR39   136 AICHPFRYKAVSGPCQVKLLIGFVWVTSALVALPLLFAMGTEYP LVNVPSHRGL  189
hFM-3    139 AVVHPLQARSMVTRAHVRRVLGAMWGLAMLCSLPNTSLHGIRQ-------LHVP   185
mFM-3    139 AVVRPLQAKSVMTRAHVRRMVGAIWVLATLFSLPNTSLHGLSQ--------LTVP  185
```

FIG. 3A

```
hNT-R1   220 GGLVCTPTIHTATVKVMIQVNIFMSFIFPMVVISVLNTIIANKLTVMVRQAAEQG-       274
rNT-R2   190 PASRVCTVLVSRATLQVFIQVNVLVSFALPLALTAFLNGITVNHLMALYSQVPSAS       245
hGHS-R   193 --------------WDTN----------------------ECRPIEFAVRSGLLTV       212
hGPR38   195 ARIASSPLASSPPLWLSRAPPPSPPSG--PETAEAAALFSRECRPS--PAQLGALRV    247
hGPR39   190 TCNRSSTRHHEQPETSNMSICINLSSRWTVFQSSIFGAFVVY-LVWLLS-----VA     239
hFM-3    186 CR----------------------G--PVPDSAVCMLVR---PRALYNMVQTTA       213
mFM-3    186 CR----------------------G--PVPDSAICSLVG---PMDFYKLVVLTTA     213 hNT-R1   275 QVCTMGGE-----------------HSTFSMAI--------EPGRVQAL---        298
rNT-R2   246 AQVSSIPSR---LELLSEEGLLGFIT---WRKTLSLGVQASLVRHKDASQIRSL-- 293
hGHS-R   213 MV-WVSSIFFFLPVFCLTVLYSLIGRKLWRRRRGDAVVGAS---------------  252
hGPR38   248 ML-WMTTAYFFLPFLCLSILYGLIGRELWSSRRPLRGPAAS---------------  287
hGPR39   240 FMCWNMMQ---VLMKSQKG-----------SLAGGTRPPQLRKSESEESRTA---   277
hFM-3    214 LL------FFCLPMAIMSVLYLLIGLRLRRERLLLMQEAKG-RGSAAARSRYTCRL  262
mFM-3    214 LL------FFCLPMVTISVLYLLIGLRLRRERMLLQVEVKG-RKTAATQETSHRRI  262 hNT-R1   299 ------RHGVRV-LRAVVIAFVVCWLPYHVRRLMFCYISDEQWTPFLYDFYHYFYM  347
rNT-R2   294 ------QHSAQV-LRAIVAVYVICWLPYHARRLMYCYIPDGWTNELYDFYHYFY    341
hGHS-R   253 -LRDQNHKQTVKMLAVVVFAFILCWLPFHVGRYLFS-KSFEPGSLEIAQISQYCNL  306
hGPR38   288 -GRERGHRQTVRVLLVVVLAFIICWLPFHVGRIIYI-NT-EDSRMMY--FSQYFNI  338
hGPR39   278 ------RRQTIIFLRLIVVTLAVCWMPNQIRRIMAAAKPKHDWTRSYFRAYMILLP  327
hFM-3    263 QQHDRGRRQVTKMLFVLVVVFGICWAPFHADRMWWS-VV-SQWTDGLHLAFQHVHV  316
mFM-3    263 QLQDRGRRQVTKMLFALVVVFGICWAPFHADRIMWS-LVYGHSIEGLHLAYQCVHI  317 hNT-R1   348 VTNALFYMSSTINPILYNLVSANFRHIFLATLAC-----------------      381
rNT-R2   342 MVTNLFYVSSAVTPILYNAVSSSFRKLFLESLGS-----------------      376
hGHS-R   307 VSFVLFYLSAAINPILYNIMSKKYRVAVFRLL------------------       338
hGPR38   339 VALQLFYLSASINPILYNLISKKYRAAAFKLL---LA-----------------   372
hGPR39   328 FSETFFYLSSVINPLLYTVSSQQFRRVFVQVLQQRLSLQHANHEKRLRVHAHSTTD 383
hFM-3    317 ISGIFFYLGSAANPVLYSLVSSRFRETFQEALC--LGA-----------------  352
mFM-3    318 ASGIFFYLGSAANPVLYSLMSTRFRETFLQALG--LGTQ----------------  354 hNT-R1   382 --------LCPVWRRRRKR------PAFSRKADSVSSNHTLSSNATRETL       417
rNT-R2   377 --------LCGEQHSLVPL------PQEAPESTTSIYSFRLWCSPRNPSLGEI    415
hGHS-R   339 --------------------GFEPFSQR KLSTLKDESSRAWTESSI           364
hGPR38   373 -----------RKSRPR--------GFHRSRDTAGEVAGDTGGDTVGYTETSA   406
hGPR39   384 SARFVQRPLLFASRRQSSARRTEKIFLSTFQSEAEPQSKSQSLSLESLEPNSGAKP 439
hFM-3    353           CCHRLRPR-------HSSHSLSRMTTGSTLCDVGSLGSWVHPL    388
mFM-3    355 --------CCHRRQPY-------HCSHNHIRLTTGSTLCDVGHRNSRDEPL       390
```

FIG. 3B

```
hNT-R1   418  ----------Y       418
rNT-R2   416  Q---------        417
hGHS-R   365  NT--------        366
hGPR38   407  NVKT------MG      413
hGPR39   440  ANSAAENGFQEHEV-   454
hFM-3    389  AGNDGPEAQQETDPS   404
mFM-3    391  AVNEDPGCQQETDPS   406
```

FIG. 3C

SEQUENCE LISTING

<160> NUMBER OF SEQ ID NOS: 11

<210> SEQ ID NO 1
<211> LENGTH: 1526
<212> TYPE: DNA
<213> ORGANISM: Mus musculus

<400> SEQUENCE: 1

```
acctgcctgc ctcagcttcc ttcgcgttgg gattaaagct gcgcactacc actgcccggc        60
caattttatt attttcaagg tttgcactcc gaatactctg tagttgaaat gcactttagt       120
gggtggcaga tgctttcttt cccagtggca tgtgactaat cagtcctcta cagtgtgata       180
acttaggaca gagctgggat tacctaaatg acttctgggt atctccccct tctatcctac       240
agactcctcc ctgcctcaat tgttccatct ttcctggagc gctctcccca aatgcttcaa       300
ggagccccat ggtctgcaat atcagtgagt tcaagtggcc ctatcaacct gaggatctga       360
accttaccga tgaggccctg aggctgaagt atttggggcc acagcagatg aaacagtttg       420
tccccatctg tgtcacgtac ctgctgatct tcgtggtggg cactctgggc aacgggctga       480
cctgcaccgt catcctgcgc aacaagacta tgcgcacgcc caccaacttc tacctcttca       540
gcctcgctgt gtccgatatg ctggtgctcc tggtgggctt gcctctggag ctttatgaga       600
tgcagcaaaa ttacccgttc cagctgggtg cgagtgcctg ctacttccga atactgctct       660
tagagaccgt ctgcctagct tcagtgctca atgtcacagc cctgagtgtg gagcgttatg       720
tggccgtggt gcgcccactc caagccaagt ctgtgatgac acgggcccat gtgcgccgca       780
tggtgggggc catctgggtc ctcgctactc tcttctctct gcccaacacc agcctgcatg       840
```

-continued

```
gcctcagtca actaactgtg ccctgccggg ggccggtgcc cgactcagct atatgttcgc    900
tggtgggtcc catggacttc tacaagttgg tggtactgac taccgcactg ctcttcttct    960
gtctgcccat ggtcaccatc agtgtgctgt atctgctcat tgggctgcgg ctgcggaggg   1020
agaggatgtt gctccaagtg gaggtcaagg gcaggaaaac cgcagcaacc caggagacct   1080
cccacagaag gattcagctg caagataggg acggagacag gtgaccaag atgctgtttg   1140 cactggttgt ggtattcggc atctgctggg ctccattcca tgctgaccgt atcatgtgga   1200
gcctggtgta tggacactca acggaaggcc tgcacctggc ctaccagtgt gtccacattg   1260
cctctggcat cttcttctat ctcggctcag cagccaaccc ggtgctctac agcctcatgt   1320
ctactcgctt ccgagagacc ttcctgcaag ccctgggcct tggaacccag tgctgtcatc   1380
gccgccaacc ctatcatggc tcccataacc acatcaggtt gaccacaggc agcaccctgt   1440
gtgacgtggg ccacaggaac agcagggacg aacctctggc tgtgaatgag gatccagggt   1500
gtcagcaaga gacagacccc tcctga                                        1526
```

<210> SEQ ID NO 2
<211> LENGTH: 405
<212> TYPE: PRT
<213> ORGANISM: Mus musculus

<400> SEQUENCE: 2

```
Met Val Cys Asn Ile Ser Glu Phe Lys Trp Pro Tyr Gln Pro Glu Asp
 1               5                  10                  15

Leu Asn Leu Thr Asp Glu Ala Leu Arg Leu Lys Tyr Leu Gly Pro Gln
             20                  25                  30

Gln Met Lys Gln Phe Val Pro Ile Cys Val Thr Tyr Leu Leu Ile Phe
         35                  40                  45

Val Val Gly Thr Leu Gly Asn Gly Leu Thr Cys Thr Val Ile Leu Arg
     50                  55                  60

Asn Lys Thr Met Arg Thr Pro Thr Asn Phe Tyr Leu Phe Ser Leu Ala
 65                  70                  75                  80

Val Ser Asp Met Leu Val Leu Val Gly Leu Pro Leu Glu Leu Tyr
                 85                  90                  95

Glu Met Gln Gln Asn Tyr Pro Phe Gln Leu Gly Ala Ser Ala Cys Tyr
            100                 105                 110

Phe Arg Ile Leu Leu Leu Glu Thr Val Cys Leu Ala Ser Val Leu Asn
        115                 120                 125

Val Thr Ala Leu Ser Val Glu Arg Tyr Val Ala Val Arg Pro Leu
    130                 135                 140

Gln Ala Lys Ser Val Met Thr Arg Ala His Val Arg Arg Met Val Gly
145                 150                 155                 160

Ala Ile Trp Val Leu Ala Thr Leu Phe Ser Leu Pro Asn Thr Ser Leu
                165                 170                 175

His Gly Leu Ser Gln Leu Thr Val Pro Cys Arg Gly Pro Val Pro Asp
            180                 185                 190

Ser Ala Ile Cys Ser Leu Val Gly Pro Met Asp Phe Tyr Lys Leu Val
        195                 200                 205

Val Leu Thr Thr Ala Leu Leu Phe Phe Cys Leu Pro Met Val Thr Ile
    210                 215                 220

Ser Val Leu Tyr Leu Leu Ile Gly Leu Arg Leu Arg Arg Glu Arg Met
225                 230                 235                 240

Leu Leu Gln Val Glu Val Lys Gly Arg Lys Thr Ala Ala Thr Gln Glu
                245                 250                 255
```

```
Thr Ser His Arg Arg Ile Gln Leu Gln Asp Arg Gly Arg Arg Gln Val
            260                 265                 270
Thr Lys Met Leu Phe Ala Leu Val Val Val Phe Gly Ile Cys Trp Ala
        275                 280                 285
Pro Phe His Ala Asp Arg Ile Met Trp Ser Leu Val Tyr Gly His Ser
    290                 295                 300
Thr Glu Gly Leu His Leu Ala Tyr Gln Cys Val His Ile Ala Ser Gly
305                 310                 315                 320
Ile Phe Phe Tyr Leu Gly Ser Ala Ala Asn Pro Val Leu Tyr Ser Leu
                325                 330                 335
Met Ser Thr Arg Phe Arg Glu Thr Phe Leu Gln Ala Leu Gly Leu Gly
            340                 345                 350
Thr Gln Cys Cys His Arg Arg Gln Pro Tyr His Gly Ser His Asn His
        355                 360                 365
Ile Arg Leu Thr Thr Gly Ser Thr Leu Cys Asp Val Gly His Arg Asn
    370                 375                 380
Ser Arg Asp Glu Pro Leu Ala Val Asn Glu Asp Pro Gly Cys Gln Gln
385                 390                 395                 400
Glu Thr Asp Pro Ser
                405

<210> SEQ ID NO 3
<211> LENGTH: 1212
<212> TYPE: DNA
<213> ORGANISM: Homo sapiens

<400> SEQUENCE: 3
atggcttgca atggcagtgc ggccaggggg cactttgacc ctgaggactt gaacctgact      60
gacgaggcac tgagactcaa gtacctgggg ccccagcaga cagagctgtt catgcccatc     120
tgtgccacat acctgctgat cttcgtggtg ggcgctgtgg caatgggct  gacctgtctg     180
gtcatcctgc ccacaaggc  catgcgcacg cctaccaact actacctctt cagcctggcc     240
gtgtcggacc tgctggtgct gctggtgggc ctgcccctgg agctctatga gatgtggcac     300
aactacccct cctgctggg  cgttggtggc tgctatttcc gcacgctact gtttgagatg     360
gtctgcctgg cctcagtgct caacgtcact gccctgagcg tggaacgcta tgtggccgtg     420
gtgcacccac tccaggccag gtccatggtg acgcgggccc atgtgcgccg agtgcttggg     480
gccgtctggg gtcttgccat gctctgctcc ctgcccaaca ccagcctgca cggcatccgg     540
cagctgcacg tgccctgccg gggcccagtg ccagactcag ctgtttgcat gctggtccgc     600
ccacgggccc tctacaacat ggtagtgcag accaccgcgc tgctcttctt ctgcctgccc     660
atggccatca tgagcgtgct ctacctgctc attgggctgc gactgcggcg ggagaggctg     720
ctgctcatgc aggaggccaa gggcaggggc tctgcagcag ccaggtccag atacacctgc     780
aggctccagc agcacgatcg gggccggaga caagtgacca agatgctgtt tgtcctggtc     840
gtggtgtttg gcatctgctg gccccgttc  acgccgacc  cgtcatgtg  gagcgtcgtg     900
tcacagtgga cagatggcct gcacctggcc ttccagcacg tgcacgtcat ctccggcatc     960
ttcttctacc tgggctcggc ggccaacccc gtgctctata gctcatgtc  cagccgcttc    1020
cgagagacct tccaggaggc cctgtgcctc ggggcctgct gccatcgcct cagaccccgc    1080
cacagctccc acagcctcag caggatgacc acaggcagca ccctgtgtga tgtgggctcc    1140
ctgggcagct gggtccaccc cctggctggg aacgatggcc cagaggcgca gcaagagacc    1200
```
gatccatcct ga                                                          1212

<210> SEQ ID NO 4
<211> LENGTH: 403
<212> TYPE: PRT
<213> ORGANISM: Homo sapiens

<400> SEQUENCE: 4

```
Met Ala Cys Asn Gly Ser Ala Ala Arg Gly His Phe Asp Pro Glu Asp
 1               5                  10                  15

Leu Asn Leu Thr Asp Glu Ala Leu Arg Leu Lys Tyr Leu Gly Pro Gln
            20                  25                  30

Gln Thr Glu Leu Phe Met Pro Ile Cys Ala Thr Tyr Leu Leu Ile Phe
        35                  40                  45

Val Val Gly Ala Val Gly Asn Gly Leu Thr Cys Leu Val Ile Leu Arg
    50                  55                  60

His Lys Ala Met Arg Thr Pro Thr Asn Tyr Tyr Leu Phe Ser Leu Ala
65                  70                  75                  80

Val Ser Asp Leu Leu Val Leu Leu Val Gly Leu Pro Leu Glu Leu Tyr
                85                  90                  95

Glu Met Trp His Asn Tyr Pro Phe Leu Leu Gly Val Gly Gly Cys Tyr
                100                 105                 110

Phe Arg Thr Leu Leu Phe Glu Met Val Cys Leu Ala Ser Val Leu Asn
            115                 120                 125

Val Thr Ala Leu Ser Val Glu Arg Tyr Val Ala Val His Pro Leu
        130                 135                 140

Gln Ala Arg Ser Met Val Thr Arg Ala His Val Arg Arg Val Leu Gly
145                 150                 155                 160

Ala Val Trp Gly Leu Ala Met Leu Cys Ser Leu Pro Asn Thr Ser Leu
                165                 170                 175

His Gly Ile Arg Gln Leu His Val Pro Cys Arg Gly Pro Val Pro Asp
                180                 185                 190

Ser Ala Val Cys Met Leu Val Arg Pro Arg Ala Leu Tyr Asn Met Val
                195                 200                 205

Val Gln Thr Thr Ala Leu Leu Phe Phe Cys Leu Pro Met Ala Ile Met
        210                 215                 220

Ser Val Leu Tyr Leu Leu Ile Gly Leu Arg Leu Arg Arg Glu Arg Leu
225                 230                 235                 240

Leu Leu Met Gln Glu Ala Lys Gly Arg Gly Ser Ala Ala Ala Arg Ser
                245                 250                 255

Arg Tyr Thr Cys Arg Leu Gln Gln His Asp Arg Gly Arg Arg Gln Val
                260                 265                 270

Thr Lys Met Leu Phe Val Leu Val Val Phe Gly Ile Cys Trp Ala
        275                 280                 285

Pro Phe His Ala Asp Arg Val Met Trp Ser Val Val Ser Gln Trp Thr
        290                 295                 300

Asp Gly Leu His Leu Ala Phe Gln His Val His Val Ile Ser Gly Ile
305                 310                 315                 320

Phe Phe Tyr Leu Gly Ser Ala Ala Asn Pro Val Leu Tyr Ser Leu Met
                325                 330                 335

Ser Ser Arg Phe Arg Glu Thr Phe Gln Glu Ala Leu Cys Leu Gly Ala
                340                 345                 350

Cys Cys His Arg Leu Arg Pro Arg His Ser Ser His Ser Leu Ser Arg
            355                 360                 365
```

```
Met Thr Thr Gly Ser Thr Leu Cys Asp Val Gly Ser Leu Gly Ser Trp
    370             375             380

Val His Pro Leu Ala Gly Asn Asp Gly Pro Glu Ala Gln Gln Glu Thr
385             390             395             400

Asp Pro Ser

<210> SEQ ID NO 5
<211> LENGTH: 418
<212> TYPE: PRT
<213> ORGANISM: Homo sapiens

<400> SEQUENCE: 5

Met Arg Leu Asn Ser Ser Ala Pro Gly Thr Pro Gly Thr Pro Ala Ala
1               5                   10                  15

Asp Pro Phe Gln Arg Ala Gln Ala Gly Leu Glu Glu Ala Leu Leu Ala
                20                  25                  30

Pro Gly Phe Gly Asn Ala Ser Gly Asn Ala Ser Glu Arg Val Leu Ala
            35                  40                  45

Ala Pro Ser Ser Glu Leu Asp Val Asn Thr Asp Ile Tyr Ser Lys Val
        50                  55                  60

Leu Val Thr Ala Val Tyr Leu Ala Leu Phe Val Val Gly Thr Val Gly
65                  70                  75                  80

Asn Thr Val Thr Ala Phe Thr Leu Ala Arg Lys Lys Ser Leu Gln Ser
                85                  90                  95

Leu Gln Ser Thr Val His Tyr His Leu Gly Ser Leu Ala Leu Ser Asp
            100                 105                 110

Leu Leu Thr Leu Leu Leu Ala Met Pro Val Glu Leu Tyr Asn Phe Ile
        115                 120                 125

Trp Val His His Pro Trp Ala Phe Gly Asp Ala Gly Cys Arg Gly Tyr
130                 135                 140

Tyr Phe Leu Arg Asp Ala Cys Thr Tyr Ala Thr Ala Leu Asn Val Ala
145                 150                 155                 160

Ser Leu Ser Val Glu Arg Tyr Leu Ala Ile Cys His Pro Phe Lys Ala
                165                 170                 175

Lys Thr Leu Met Ser Arg Ser Arg Thr Lys Lys Phe Ile Ser Ala Ile
            180                 185                 190

Trp Leu Ala Ser Ala Leu Leu Thr Val Pro Met Leu Phe Thr Met Gly
        195                 200                 205

Glu Gln Asn Arg Ser Ala Asp Gly Gln His Ala Gly Gly Leu Val Cys
210                 215                 220

Thr Pro Thr Ile His Thr Ala Thr Val Lys Val Val Ile Gln Val Asn
225                 230                 235                 240

Thr Phe Met Ser Phe Ile Phe Pro Met Val Val Ile Ser Val Leu Asn
                245                 250                 255

Thr Ile Ile Ala Asn Lys Leu Thr Val Met Val Arg Gln Ala Ala Glu
            260                 265                 270

Gln Gly Gln Val Cys Thr Val Gly Gly Glu His Ser Thr Phe Ser Met
        275                 280                 285

Ala Ile Glu Pro Gly Arg Val Gln Ala Leu Arg His Gly Val Arg Val
290                 295                 300

Leu Arg Ala Val Val Ile Ala Phe Val Val Cys Trp Leu Pro Tyr His
305                 310                 315                 320

Val Arg Arg Leu Met Phe Cys Tyr Ile Ser Asp Glu Gln Trp Thr Pro
                325                 330                 335
```

-continued

```
Phe Leu Tyr Asp Phe Tyr His Tyr Phe Tyr Met Val Thr Asn Ala Leu
            340                 345                 350

Phe Tyr Val Ser Ser Thr Ile Asn Pro Ile Leu Tyr Asn Leu Val Ser
        355                 360                 365

Ala Asn Phe Arg His Ile Phe Leu Ala Thr Leu Ala Cys Leu Cys Pro
    370                 375                 380

Val Trp Arg Arg Arg Lys Arg Pro Ala Phe Ser Arg Lys Ala Asp
385                 390                 395                 400

Ser Val Ser Ser Asn His Thr Leu Ser Ser Asn Ala Thr Arg Glu Thr
                405                 410                 415

Leu Tyr

<210> SEQ ID NO 6
<211> LENGTH: 415
<212> TYPE: PRT
<213> ORGANISM: Rattus norvegicus

<400> SEQUENCE: 6

Met Glu Thr Ser Ser Pro Trp Pro Pro Arg Pro Ser Pro Ser Ala Gly
  1               5                  10                  15

Leu Ser Leu Glu Ala Arg Leu Gly Val Asp Thr Arg Leu Trp Ala Lys
             20                  25                  30

Val Leu Phe Thr Ala Leu Tyr Ser Leu Ile Phe Ala Phe Gly Thr Ala
         35                  40                  45

Gly Asn Ala Leu Ser Val His Val Val Leu Lys Ala Arg Ala Gly Arg
     50                  55                  60

Pro Gly Arg Leu Arg Tyr His Val Leu Ser Leu Ala Leu Ser Ala Leu
 65                  70                  75                  80

Leu Leu Leu Leu Val Ser Met Pro Met Glu Leu Tyr Asn Phe Val Trp
                 85                  90                  95

Ser His Tyr Pro Trp Val Phe Gly Asp Leu Gly Cys Arg Gly Tyr Tyr
            100                 105                 110

Phe Val Arg Glu Leu Cys Ala Tyr Ala Thr Val Leu Ser Val Ala Ser
        115                 120                 125

Leu Ser Ala Glu Arg Cys Leu Ala Val Cys Gln Pro Leu Arg Ala Arg
    130                 135                 140

Arg Leu Leu Thr Pro Arg Arg Thr Arg Arg Leu Leu Ser Leu Val Trp
145                 150                 155                 160

Val Ala Ser Leu Gly Leu Ala Leu Pro Met Ala Val Ile Met Gly Gln
                165                 170                 175

Lys His Glu Val Glu Ser Ala Asp Gly Glu Pro Glu Pro Ala Ser Arg
            180                 185                 190

Val Cys Thr Val Leu Val Ser Arg Ala Thr Leu Gln Val Phe Ile Gln
        195                 200                 205

Val Asn Val Leu Val Ser Phe Ala Leu Pro Leu Ala Leu Thr Ala Phe
    210                 215                 220

Leu Asn Gly Ile Thr Val Asn His Leu Met Ala Leu Tyr Ser Gln Val
225                 230                 235                 240

Pro Ser Ala Ser Ala Gln Val Ser Ser Ile Pro Ser Arg Leu Glu Leu
                245                 250                 255

Leu Ser Glu Glu Gly Leu Leu Gly Phe Ile Thr Trp Arg Lys Thr Leu
            260                 265                 270

Ser Leu Gly Val Gln Ala Ser Leu Val Arg His Lys Asp Ala Ser Gln
        275                 280                 285
```

```
Ile Arg Ser Leu Gln His Ser Ala Gln Val Leu Arg Ala Ile Val Ala
    290                 295                 300

Val Tyr Val Ile Cys Trp Leu Pro Tyr His Ala Arg Arg Leu Met Tyr
305                 310                 315                 320

Cys Tyr Ile Pro Asp Asp Gly Trp Thr Asn Glu Leu Tyr Asp Phe Tyr
                325                 330                 335

His Tyr Phe Tyr Met Val Thr Asn Thr Leu Phe Tyr Val Ser Ser Ala
            340                 345                 350

Val Thr Pro Ile Leu Tyr Asn Ala Val Ser Ser Phe Arg Lys Leu
        355                 360                 365

Phe Leu Glu Ser Leu Gly Ser Leu Cys Gly Glu Gln His Ser Leu Val
    370                 375                 380

Pro Leu Pro Gln Glu Ala Pro Glu Ser Thr Thr Ser Thr Tyr Ser Phe
385                 390                 395                 400

Arg Leu Trp Gly Ser Pro Arg Asn Pro Ser Leu Gly Glu Ile Gln
                405                 410                 415

<210> SEQ ID NO 7
<211> LENGTH: 366
<212> TYPE: PRT
<213> ORGANISM: Homo sapiens

<400> SEQUENCE: 7

Met Trp Asn Ala Thr Pro Ser Glu Glu Pro Gly Phe Asn Leu Thr Leu
1               5                   10                  15

Ala Asp Leu Asp Trp Asp Ala Ser Pro Gly Asn Asp Ser Leu Gly Asp
            20                  25                  30

Glu Leu Leu Gln Leu Phe Pro Ala Pro Leu Leu Ala Gly Val Thr Ala
        35                  40                  45

Thr Cys Val Ala Leu Phe Val Val Gly Ile Ala Gly Asn Leu Leu Thr
    50                  55                  60

Met Leu Val Val Ser Arg Phe Arg Glu Leu Arg Thr Thr Thr Asn Leu
65                  70                  75                  80

Tyr Leu Ser Ser Met Ala Phe Ser Asp Leu Leu Ile Phe Leu Cys Met
                85                  90                  95

Pro Leu Asp Leu Val Arg Leu Trp Gln Tyr Arg Pro Trp Asn Phe Gly
            100                 105                 110

Asp Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
    130                 135                 140

Ile Cys Phe Pro Leu Arg Ala Lys Val Val Thr Lys Gly Arg Val
145                 150                 155                 160

Lys Leu Val Ile Phe Val Ile Trp Ala Val Ala Phe Cys Ser Ala Gly
                165                 170                 175

Pro Ile Phe Val Leu Val Gly Val Glu His Glu Asn Gly Thr Asp Pro
            180                 185                 190

Trp Asp Thr Asn Glu Cys Arg Pro Thr Glu Phe Ala Val Arg Ser Gly
        195                 200                 205

Leu Leu Thr Val Met Val Trp Val Ser Ser Ile Phe Phe Phe Leu Pro
    210                 215                 220

Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255
```

-continued

```
Asn His Lys Gln Thr Val Lys Met Leu Ala Val Val Phe Ala Phe
            260                 265                 270

Ile Leu Cys Trp Leu Pro Phe His Val Gly Arg Tyr Leu Phe Ser Lys
            275                 280                 285

Ser Phe Glu Pro Gly Ser Leu Glu Ile Ala Gln Ile Ser Gln Tyr Cys
        290                 295                 300

Asn Leu Val Ser Phe Val Leu Phe Tyr Leu Ser Ala Ala Ile Asn Pro
305                 310                 315                 320

Ile Leu Tyr Asn Ile Met Ser Lys Lys Tyr Arg Val Ala Val Phe Arg
                325                 330                 335

Leu Leu Gly Phe Glu Pro Phe Ser Gln Arg Lys Leu Ser Thr Leu Lys
            340                 345                 350

Asp Glu Ser Ser Arg Ala Trp Thr Glu Ser Ser Ile Asn Thr
            355                 360                 365

<210> SEQ ID NO 8
<211> LENGTH: 412
<212> TYPE: PRT
<213> ORGANISM: Homo sapiens

<400> SEQUENCE: 8

Met Gly Ser Pro Trp Asn Gly Ser Asp Gly Pro Glu Gly Ala Arg Glu
1               5                   10                  15

Pro Pro Trp Pro Ala Leu Pro Pro Cys Asp Glu Arg Arg Cys Ser Pro
            20                  25                  30

Phe Pro Leu Gly Ala Leu Val Pro Val Thr Ala Val Cys Leu Cys Leu
        35                  40                  45

Phe Val Val Gly Val Ser Gly Asn Val Val Thr Val Met Leu Ile Gly
    50                  55                  60

Arg Tyr Arg Asp Met Arg Thr Thr Thr Asn Leu Tyr Leu Gly Ser Met
65                  70                  75                  80

Ala Val Ser Asp Leu Leu Ile Leu Leu Gly Leu Pro Phe Asp Leu Tyr
                85                  90                  95

Arg Leu Trp Arg Ser Arg Pro Trp Val Phe Gly Pro Leu Leu Cys Arg
            100                 105                 110

Leu Ser Leu Tyr Val Gly Glu Gly Cys Thr Tyr Ala Thr Leu Leu His
        115                 120                 125

Met Thr Ala Leu Ser Val Glu Arg Tyr Leu Ala Ile Cys Arg Pro Leu
    130                 135                 140

Arg Ala Arg Val Leu Val Thr Arg Arg Val Arg Ala Leu Ile Ala
145                 150                 155                 160

Val Leu Trp Ala Val Ala Leu Leu Ser Ala Gly Pro Phe Leu Phe Leu
                165                 170                 175

Val Gly Val Glu Gln Asp Pro Gly Ile Ser Val Val Pro Gly Leu Asn
            180                 185                 190

Gly Thr Ala Arg Ile Ala Ser Ser Pro Leu Ala Ser Ser Pro Pro Leu
        195                 200                 205

Trp Leu Ser Arg Ala Pro Pro Pro Ser Pro Pro Ser Gly Pro Glu Thr
    210                 215                 220

Ala Glu Ala Ala Ala Leu Phe Ser Arg Glu Cys Arg Pro Ser Pro Ala
225                 230                 235                 240

Gln Leu Gly Ala Leu Arg Val Met Leu Trp Val Thr Thr Ala Tyr Phe
                245                 250                 255

Phe Leu Pro Phe Leu Cys Leu Ser Ile Leu Tyr Gly Leu Ile Gly Arg
```

```
                     260                 265                 270
Glu Leu Trp Ser Ser Arg Arg Pro Leu Arg Gly Pro Ala Ala Ser Gly
            275                 280                 285

Arg Glu Arg Gly His Arg Gln Thr Val Arg Val Leu Leu Val Val Val
290                 295                 300

Leu Ala Phe Ile Ile Cys Trp Leu Pro Phe His Val Gly Arg Ile Ile
305                 310                 315                 320

Tyr Ile Asn Thr Glu Asp Ser Arg Met Met Tyr Phe Ser Gln Tyr Phe
                325                 330                 335

Asn Ile Val Ala Leu Gln Leu Phe Tyr Leu Ser Ala Ser Ile Asn Pro
                340                 345                 350

Ile Leu Tyr Asn Leu Ile Ser Lys Lys Tyr Arg Ala Ala Ala Phe Lys
                355                 360                 365

Leu Leu Leu Ala Arg Lys Ser Arg Pro Arg Gly Phe His Arg Ser Arg
            370                 375                 380

Asp Thr Ala Gly Glu Val Ala Gly Asp Thr Gly Gly Asp Thr Val Gly
385                 390                 395                 400

Tyr Thr Glu Thr Ser Ala Asn Val Lys Thr Met Gly
                405                 410

<210> SEQ ID NO 9
<211> LENGTH: 453
<212> TYPE: PRT
<213> ORGANISM: Homo sapiens

<400> SEQUENCE: 9

Met Ala Ser Pro Ser Leu Pro Gly Ser Asp Cys Ser Gln Ile Ile Asp
1               5                   10                  15

His Ser His Val Pro Glu Phe Glu Val Ala Thr Trp Ile Lys Ile Thr
                20                  25                  30

Leu Ile Leu Val Tyr Leu Ile Ile Phe Val Met Gly Leu Leu Gly Asn
            35                  40                  45

Ser Ala Thr Ile Arg Val Thr Gln Val Leu Gln Lys Lys Gly Tyr Leu
        50                  55                  60

Gln Lys Glu Val Thr Asp His Met Val Ser Leu Ala Cys Ser Asp Ile
65                  70                  75                  80

Leu Val Phe Leu Ile Gly Met Pro Met Glu Phe Tyr Ser Ile Ile Trp
                85                  90                  95

Asn Pro Leu Thr Thr Ser Ser Tyr Thr Leu Ser Cys Lys Leu His Thr
                100                 105                 110

Phe Leu Phe Glu Ala Cys Ser Tyr Ala Thr Leu Leu His Val Leu Thr
            115                 120                 125

Leu Ser Phe Glu Arg Tyr Ile Ala Ile Cys His Pro Phe Arg Tyr Lys
130                 135                 140

Ala Val Ser Gly Pro Cys Gln Val Lys Leu Leu Ile Gly Phe Val Trp
145                 150                 155                 160

Val Thr Ser Ala Leu Val Ala Leu Pro Leu Leu Phe Ala Met Gly Thr
                165                 170                 175

Glu Tyr Pro Leu Val Asn Val Pro Ser His Arg Gly Leu Thr Cys Asn
                180                 185                 190

Arg Ser Ser Thr Arg His His Glu Gln Pro Glu Thr Ser Asn Met Ser
            195                 200                 205

Ile Cys Thr Asn Leu Ser Ser Arg Trp Thr Val Phe Gln Ser Ser Ile
210                 215                 220
```

```
Phe Gly Ala Phe Val Val Tyr Leu Val Leu Leu Ser Val Ala Phe
225                 230                 235                 240

Met Cys Trp Asn Met Met Gln Val Leu Met Lys Ser Gln Lys Gly Ser
            245                 250                 255

Leu Ala Gly Gly Thr Arg Pro Pro Gln Leu Arg Lys Ser Glu Ser Glu
                260                 265                 270

Glu Ser Arg Thr Ala Arg Arg Gln Thr Ile Ile Phe Leu Arg Leu Ile
        275                 280                 285

Val Val Thr Leu Ala Val Cys Trp Met Pro Asn Gln Ile Arg Arg Ile
    290                 295                 300

Met Ala Ala Lys Pro Lys His Asp Trp Thr Arg Ser Tyr Phe Arg
305                 310                 315                 320

Ala Tyr Met Ile Leu Leu Pro Phe Ser Glu Thr Phe Phe Tyr Leu Ser
                325                 330                 335

Ser Val Ile Asn Pro Leu Leu Tyr Thr Val Ser Ser Gln Gln Phe Arg
                340                 345                 350

Arg Val Phe Val Gln Val Leu Cys Cys Arg Leu Ser Leu Gln His Ala
                355                 360                 365

Asn His Glu Lys Arg Leu Arg Val His Ala His Ser Thr Thr Asp Ser
            370                 375                 380

Ala Arg Phe Val Gln Arg Pro Leu Leu Phe Ala Ser Arg Arg Gln Ser
385                 390                 395                 400

Ser Ala Arg Arg Thr Glu Lys Ile Phe Leu Ser Thr Phe Gln Ser Glu
                405                 410                 415

Ala Glu Pro Gln Ser Lys Ser Gln Ser Leu Ser Leu Glu Ser Leu Glu
                420                 425                 430

Pro Asn Ser Gly Ala Lys Pro Ala Asn Ser Ala Ala Glu Asn Gly Phe
            435                 440                 445

Gln Glu His Glu Val
        450

<210> SEQ ID NO 10
<211> LENGTH: 403
<212> TYPE: PRT
<213> ORGANISM: Homo sapiens

<400> SEQUENCE: 10

Met Ala Cys Asn Gly Ser Ala Ala Arg Gly His Phe Asp Pro Glu Asp
  1               5                  10                  15

Leu Asn Leu Thr Asp Glu Ala Leu Arg Leu Lys Tyr Leu Gly Pro Gln
                 20                  25                  30

Gln Thr Glu Leu Phe Met Pro Ile Cys Ala Thr Tyr Leu Leu Ile Phe
             35                  40                  45

Val Val Gly Ala Val Gly Asn Gly Leu Thr Cys Leu Val Ile Leu Arg
     50                  55                  60

His Lys Ala Met Arg Thr Pro Thr Asn Tyr Tyr Leu Phe Ser Leu Ala
 65                  70                  75                  80

Val Ser Asp Leu Leu Val Leu Leu Val Gly Leu Pro Leu Glu Leu Tyr
                 85                  90                  95

Glu Met Trp His Asn Tyr Pro Phe Leu Leu Gly Val Gly Gly Cys Tyr
            100                 105                 110

Phe Arg Thr Leu Leu Phe Glu Met Val Cys Leu Ala Ser Val Leu Asn
            115                 120                 125

Val Thr Ala Leu Ser Val Glu Arg Tyr Val Ala Val Val His Pro Leu
        130                 135                 140
```

-continued

```
Gln Ala Arg Ser Met Val Thr Arg Ala His Val Arg Arg Val Leu Gly
145                 150                 155                 160

Ala Val Trp Gly Leu Ala Met Leu Cys Ser Leu Pro Asn Thr Ser Leu
                165                 170                 175

His Gly Ile Arg Gln Leu His Val Pro Cys Arg Gly Pro Val Pro Asp
            180                 185                 190

Ser Ala Val Cys Met Leu Val Arg Pro Arg Ala Leu Tyr Asn Met Val
        195                 200                 205

Val Gln Thr Thr Ala Leu Leu Phe Phe Cys Leu Pro Met Ala Ile Met
    210                 215                 220

Ser Val Leu Tyr Leu Leu Ile Gly Leu Arg Leu Arg Arg Glu Arg Leu
225                 230                 235                 240

Leu Leu Met Gln Glu Ala Lys Gly Arg Gly Ser Ala Ala Arg Ser
                245                 250                 255

Arg Tyr Thr Cys Arg Leu Gln Gln His Asp Arg Gly Arg Arg Gln Val
                260                 265                 270

Thr Lys Met Leu Phe Val Leu Val Val Phe Gly Ile Cys Trp Ala
                275                 280                 285

Pro Phe His Ala Asp Arg Val Met Trp Ser Val Val Ser Gln Trp Thr
290                 295                 300

Asp Gly Leu His Leu Ala Phe Gln His Val His Val Ile Ser Gly Ile
305                 310                 315                 320

Phe Phe Tyr Leu Gly Ser Ala Ala Asn Pro Val Leu Tyr Ser Leu Met
                325                 330                 335

Ser Ser Arg Phe Arg Glu Thr Phe Gln Glu Ala Leu Cys Leu Gly Ala
                340                 345                 350

Cys Cys His Arg Leu Arg Pro Arg His Ser Ser His Ser Leu Ser Arg
                355                 360                 365

Met Thr Thr Gly Ser Thr Leu Cys Asp Val Gly Ser Leu Gly Ser Trp
                370                 375                 380

Val His Pro Leu Ala Gly Asn Asp Gly Pro Glu Ala Gln Gln Glu Thr
385                 390                 395                 400

Asp Pro Ser

<210> SEQ ID NO 11
<211> LENGTH: 405
<212> TYPE: PRT
<213> ORGANISM: Mus musculus

<400> SEQUENCE: 11

Met Val Cys Asn Ile Ser Glu Phe Lys Trp Pro Tyr Gln Pro Glu Asp
1               5                   10                  15

Leu Asn Leu Thr Asp Glu Ala Leu Arg Leu Lys Tyr Leu Gly Pro Gln
                20                  25                  30

Gln Met Lys Gln Phe Val Pro Ile Cys Val Thr Tyr Leu Leu Ile Phe
            35                  40                  45

Val Val Gly Thr Leu Gly Asn Gly Leu Thr Cys Thr Val Ile Leu Arg
        50                  55                  60

Asn Lys Thr Met Arg Thr Pro Thr Asn Phe Tyr Leu Phe Ser Leu Ala
65                  70                  75                  80

Val Ser Asp Met Leu Val Leu Val Gly Leu Pro Leu Glu Leu Tyr
                85                  90                  95

Glu Met Gln Gln Asn Tyr Pro Phe Gln Leu Gly Ala Ser Ala Cys Tyr
                100                 105                 110
```

-continued

```
Phe Arg Ile Leu Leu Glu Thr Val Cys Leu Ala Ser Val Leu Asn
        115                 120                 125

Val Thr Ala Leu Ser Val Glu Arg Tyr Val Ala Val Val Arg Pro Leu
        130                 135                 140

Gln Ala Lys Ser Val Met Thr Arg Ala His Val Arg Arg Met Val Gly
145                 150                 155                 160

Ala Ile Trp Val Leu Ala Thr Leu Phe Ser Leu Pro Asn Thr Ser Leu
                165                 170                 175

His Gly Leu Ser Gln Leu Thr Val Pro Cys Arg Gly Pro Val Pro Asp
                180                 185                 190

Ser Ala Ile Cys Ser Leu Val Gly Pro Met Asp Phe Tyr Lys Leu Val
                195                 200                 205

Val Leu Thr Thr Ala Leu Leu Phe Phe Cys Leu Pro Met Val Thr Ile
        210                 215                 220

Ser Val Leu Tyr Leu Leu Ile Gly Leu Arg Leu Arg Arg Glu Arg Met
225                 230                 235                 240

Leu Leu Gln Val Glu Val Lys Gly Arg Lys Thr Ala Ala Thr Gln Glu
                245                 250                 255

Thr Ser His Arg Arg Ile Gln Leu Gln Asp Arg Gly Arg Arg Gln Val
                260                 265                 270

Thr Lys Met Leu Phe Ala Leu Val Val Phe Gly Ile Cys Trp Ala
        275                 280                 285

Pro Phe His Ala Asp Arg Ile Met Trp Ser Leu Val Tyr Gly His Ser
        290                 295                 300

Thr Glu Gly Leu His Leu Ala Tyr Gln Cys Val His Ile Ala Ser Gly
305                 310                 315                 320

Ile Phe Phe Tyr Leu Gly Ser Ala Ala Asn Pro Val Leu Tyr Ser Leu
                325                 330                 335

Met Ser Thr Arg Phe Arg Glu Thr Phe Leu Gln Ala Leu Gly Leu Gly
                340                 345                 350

Thr Gln Cys Cys His Arg Arg Gln Pro Tyr His Gly Ser His Asn His
                355                 360                 365

Ile Arg Leu Thr Thr Gly Ser Thr Leu Cys Asp Val Gly His Arg Asn
        370                 375                 380

Ser Arg Asp Glu Pro Leu Ala Val Asn Glu Asp Pro Gly Cys Gln Gln
385                 390                 395                 400

Glu Thr Asp Pro Ser
                405
```

GROWTH HORMONE SECRETAGOGUE RELATED RECEPTORS AND NUCLEIC ACIDS

CROSS-REFERENCE TO RELATED APPLICATIONS

This application is a National stage entry of PCT/US99/15941, filed Jul. 13, 1999, which claims priority to U.S. Provisional Application Serial No. 60/092,623, filed Jul. 13, 1998, now abandoned.

FIELD OF THE INVENTION

This invention relates to a new family of receptors, growth hormone secretagogue-related receptors (GHSR-Rs), nucleic acids encoding these receptors, and to the use of these receptors to identify ligands that modulate GHSR-R function.

BACKGROUND OF THE INVENTION

Growth hormone secretagogues (GHSs) and secretagogue-like compounds, both peptide and non-peptide, bind to and exert their biological effects (i.e., release of growth hormone (GH)) through a G protein-coupled receptor (GPC-R) distinct from the receptors for growth hormone releasing hormone (GHRH) and somatostatin (SST) (Pong et al., 1996 Mol. Endocrin. 10:57–61). The molecular cloning of the growth hormone secretagogue receptor (GHS-R) capitalized on the pivotal observation that GHSs transduce their signal through activation of the phospholipase C pathway (Cheng et al., 1991 Endocrinology 129:3337–3342; Howard et al., 1996 Science 273:974–977). cDNA and genomic DNA cloning from human, swine, and rat showed that the GHS-R is a remarkably conserved protein of 364/366 acids containing 7 putative alpha-helical transmembrane (TM) domains, a signature feature of GPC-R's (Howard et al. 1996; McKee et al., 1997 Mol. Endocrin. 11:415–423). In all species evaluated, the GHS-R is encoded by a single highly-conserved gene containing one intron, placed at the C-terminal end of TM domain 5. The GHS-R exhibits the highest sequence similarity to the receptors for neurotensin (NT-R) with sequence identity of 34%. The biology of the growth hormone secretagogues (GHSs) is still in a relatively early stage of development. Research is focused on identification of the GHS natural ligand system and understanding the role of the GHS-R in brain regions (substantia nigra, dentate gyrus, hippocampus) other than those traditionally thought to be involved in GH secretion (Bennett et al. 1997; Guan et al. 1997).

The identification of other G-protein coupled receptors points to the existence of a new natural ligand pathway perhaps divergent from the neuropeptide neurotensin and the GHS natural ligand. Two new human full-length GPC-R's entitled GPR38 and GPR39 were cloned having 52% and 32% protein sequence identity to the human GHS-R, respectively (McKee et al. 1997).

It would be desirable to identify other GPC-Rs perhaps impactful on GH release and elucidate their functions. It would also be desirable to identify ligands particular to these receptors that play an important role in these and other associated pathways.

One peptide for which receptors have not been molecularly identified to date is neuromedin U. Neuromedin U (NMU) is a neuropeptide first isolated from porcine spinal cord in two molecular forms, one containing 25 amino acids (NMU-25) and the other one 8 amino acids (NMU-8); Minamino et al., 1985 Biochem Biophs Res Commun130:1078–85. It was subsequently isolated from rat (NMU-23), human (NMU-25), frog (NMU-25), dog (NMU-8 and NMU-25), rabbit (NMU-25), and chicken (NMU-25); Domin et al., 1986 Biochem Biophys Res Commun 140:1127–34; Conlon et al., 1988 J Neurochem 51:988–91; Minamino et al., 1988 Biochem Biophy Res Commun 156:355–60; Domin et al., 1989 J Biol Chem 26420881–5; O'Harte et al., 1991 Peptides 12:11–5; Kage et al., 1991 Regul Pept 33:191–8; and Domin et al., 1991 Regul Pept 41: 1–8. Mammalian NMUs share a common C-terminal sequence-Phe-Leu-Phe-Arg-Pro-Arg-Asn-amide which appears to be essential for its biological activities. NMU is distributed both in the gastrointestinal tract and the central nervous system (CNS).

In the rat, the highest concentration of NMU was found in the ileum, followed by the pituitary, hypothalamus, spinal cord, thyroid, and the genitourinary tract. Immunohistochemistry studies showed that NMU immunoreactivity in the gut was only found in nerve fibers, mainly in the myenteric and submucous plexuses, and in the mucosa of all areas except stomach while no NMU immunoreactivity was found in endocrine cells. In the rat brain, NMU immunoreactivity was found in fibers widespread throughout the brain with the exception of the cerebellum.

Human and rat genes encoding NMU precursor have been isolated. Both encode NMU at the C-terminus and other potential peptide products in the middle; Lo et al., 1992 Mol Endocrinol 6:1538–44; Austin et al., 1995 J Mol Endocrinol 14:157–69.

High affinity NMU binding was characterized in rat uterus, and was shown to be sensitive to GTP-γ-S (Nandha et al., 1993 Endocrinology 133:482–6), suggesting the receptor for NMU was a G-protein coupled receptor. However, no receptor of NMU has been molecularly identified so far.

The physiological role of NMU remains largely unrecognized. It can cause potent contraction of smooth muscle, increase arterial blood pressure, modify intestinal ion transport, and at low doses stimulates the function and growth of the adrenal cortex. NMU was also shown to reduce the blood flow in superior enteric artery and portal vein while increase blood flow slightly in pancreatic tissue. Nevertheless, NMU is the only neuromedin without a receptor cloned nor a great deal of knowledge obtained concerning its pharmacology and physiology.

It would be most desirable to identify a G-protein coupled receptor responsive to neuromedin U or ligands sufficiently similar thereto. A receptor responsive to neuromedin U would greatly facilitate our understanding of the physiological mechanisms of neuromedin U and other ligands sufficiently similar thereto.

SUMMARY OF THE INVENTION

This invention relates to a new family of G protein-coupled receptors, growth hormone secretagogue-related receptors (GHSR-Rs) free from receptor-associated proteins, which exhibit moderate protein sequence identity (33 and 29%) to both the growth hormone secretagogue receptor (GHS-R) and the neurotensin receptor (NT-R) type 1, respectively. Particularly, the full-length mouse and human GHSR-Rs have been identified. These newly identified receptors are expressed in a diverse set of tissues. A further aspect of this invention is the above receptors which are isolated or purified.

Another aspect of this invention are GHSR-Rs which are encoded by substantially the same nucleic acid sequence, but which have undergone changes in splicing or other RNA processing-derived modifications or mutagenesis induced changes, so that the expressed protein has a homologous, but different amino acid sequence from the native form. These variant forms may have different and/or additional functions in animal physiology or in vitro in cell based assays.

Growth hormone secretagogue related receptors (GHSR-Rs) are proteins containing various functional domains, including one or more domains which anchor the receptor in the cell membrane, and at least one ligand binding domain. As with many receptor proteins, it is possible to modify (e.g., by deletion) many of the amino acids, particularly those which are not found in the ligand binding domain, and still retain at least a percentage of the biological activity of the original receptor. This invention specifically includes such modified functionally equivalent GHSR-Rs as well as receptors comprising the binding domain of a GHSR-R of this invention.

Additionally, it is possible to modify other functional domains such as those that interact with second messenger effector systems, by altering binding specificity and/or selectivity. Such functionally equivalent mutant receptors are also within the scope of this invention.

Another aspect of this invention are nucleic acids which encode growth hormone secretagogue related receptors (GHSR-Rs). More specifically, the invention relates to nucleic acids comprising the sequences of SEQ ID NOs: 1 and 3 as well as those which hybridize to same under highly stringent conditions. These nucleic acids may be free from associated nucleic acids, or they may be isolated or purified. For most cloning purposes, cDNA is a preferred nucleic acid, but this invention specifically includes other forms of DNA as well as RNAs which encode a GHSR-R.

Yet another aspect of this invention relates to vectors which comprise nucleic acids encoding a GHSR-R. These vectors may be comprised of DNA or RNA; for most cloning purposes DNA vectors are preferred. Typical vectors include plasmids, modified viruses, bacteriophage and cosmids, yeast artificial chromosomes and other forms of episomal or integrated DNA that can encode a GHSR-R. It is well within the skill of the ordinary artisan to determine an appropriate vector for a particular gene transfer or other use.

A further aspect of this invention are host cells which are transformed with a gene which encodes a growth hormone secretagogue related receptor. The host cell may or may not naturally express a GHSR-R on the cell membrane. Preferably, once transformed, the host cells are able to express a growth hormone secretagogue related receptor on the cell membrane. Depending on the host cell, it may be desirable to adapt the DNA so that particular codons are used in order to optimize expression. Such adaptations are known in the art, and these nucleic acids are also included within the scope of this invention. Generally, mammalian cell lines, such as COS, HEK-293, CHO, HeLa, NS/0, CV-1, GC, GH3 or VERO cells are preferred, but other cells and cell lines such as *Xenopus oocytes* or insect cells, may also be used. Both cell lines transformed to express the GHSR-R receptor and those naturally expressing the receptor are included for use within the following assays.

One further aspect of this invention is a method of identifying ligands comprising contacting cells expressing the GHSR-R receptor in accordance with the instant invention with a compound suspected of being a ligand specific for said receptor and determining whether binding occurs, binding constituting a positive indication of the presence of a ligand.

Another aspect of this invention is a method of identifying ligands for GHSR-R which comprises contacting cells expressing the GHSR-R receptor with a compound suspected of being a ligand specific for said receptor in the presence of jelly fish aequorin or other suitable reporter responsive to $Ca^{2+}$ mobilization, and monitoring for luminescence or other signal from the reporter indicating activation of the receptor, activation constituting a positive indication of the presence of a ligand.

Another aspect of the instant invention is a method of identifying ligands for GHSR-R which comprises contacting cells expressing the GHSR-R receptor with a compound suspected of being a ligand specific for said receptor, and monitoring for changes in concentration of intracellular cyclic AMP (cAMP); an increase in cAMP constituting a positive indication of the presence of a ligand.

An additional aspect of the invention is a method for determining whether a substance is a potential agonist or antagonist of GHSR-R comprising contacting cells expressing the GHSR-R receptor with labeled neuromedin U in the presence and in the absence of the substance, and measuring the binding of neuromedin U to GHSR-R, where if the amount of binding of neuromedin U is more or less in the presence of the substance than in the absence of the substance, then the substance is a potential agonist or antagonist of GHSR-R, respectively.

A further aspect of the instant invention is a method of determining whether a substance is a potential agonist of GHSR-R which comprises contacting cells expressing the GHSR-R receptor with the substance in the presence of jelly fish aequorin or other suitable reporter responsive to $Ca^{2+}$, and monitoring for luminescence or other signal from the reporter indicating activation of the receptor; activation constituting a positive indication of the presence of an agonist.

Another aspect of the instant invention is a method of determining whether a substance is a potential antagonist of GHSR-R which comprises contacting cells expressing the GHSR-R receptor first with the substance and then with neuromedin U in the presence of jelly fish aequorin or other suitable reporter responsive to $Ca^{2+}$, and monitoring for luminescence or other signal from the reporter indicating activation of the receptor; where if the amount of luminescence or signal is less in the presence of the substance than in the absence of the substance, then the substance is a potential antagonist of GHSR-R.

Another aspect of the instant invention is a method of determining whether a substance is a potential agonist of GHSR-R which comprises contacting cells expressing the GHSR-R receptor with the substance, and monitoring for changes in cyclic AMP (cAMP); an increase in cAMP constituting a positive indication of an agonist.

Another aspect of the instant invention is a method of determining whether a substance is a potential antagonist of GHSR-R which comprises contacting cells expressing the GHSR-R receptor with the substance, and monitoring for changes in cyclic AMP (cAMP); a marginal to no increase in cAMP constituting a positive indication of an antagonist.

Another aspect of the instant invention is a method for the treatment or prevention of obesity which comprises administering to a mammal in need of such treatment or prevention an effective amount of neuromedin U or a GHSR-R agonist.

A further aspect of the instant invention is a method of decreasing food intake of a mammal which comprises administering to said mammal an effective amount of neuromedin U or a GHSR-R agonist.

Yet one further aspect of this invention is a method of determining whether a compound binds to both growth hormone secretagogue receptor (GHS-R) and growth hormone secretagogue related receptor (GHSR-R) which comprises contacting both GHS-R and GHSR-R with the compound or ligand of interest and determining whether binding occurs to both receptors.

BRIEF DESCRIPTION OF THE DRAWINGS/FIGURES

Figure 1B:
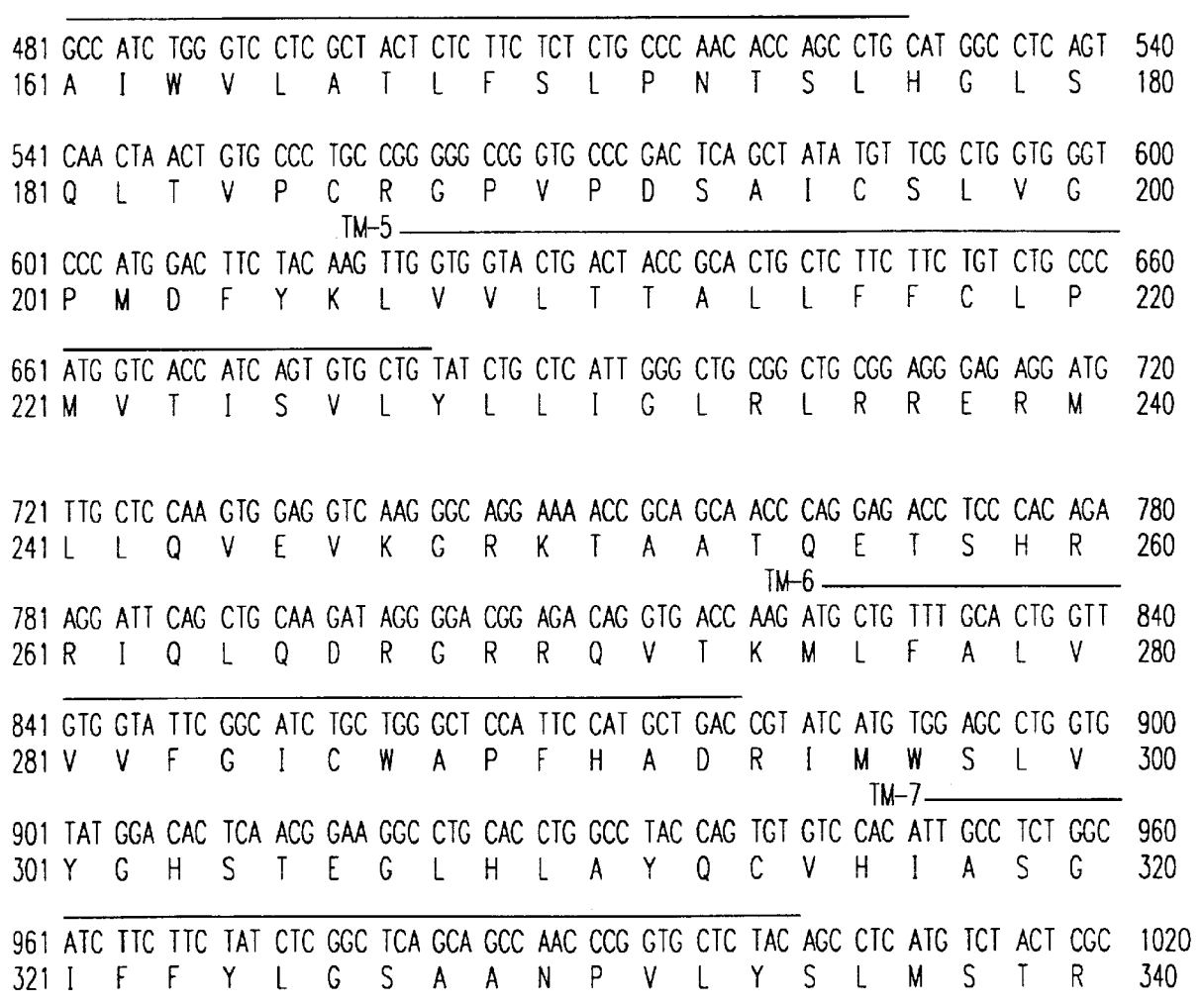

FIGS. 1A–C presents the DNA (SEQ ID NO:1) and deduced amino acid (SEQ ID NO:2) sequences for mouse GHSR-R. Putative transmembrane alpha helices are overlined and numbered from 1 to 7.

FIGS. 2A–C shows the DNA (SEQ ID NO:3) and deduced amino acid (SEQ ID NO:4) sequences for human GHSR-R. Putative transmembrane alpha helices are overlined and numbered from 1 to 7.

FIGS. 3A–C presents a comparison of the GHSR-R of the present invention to other members of the GHS-R/NT-R Family.

Figure 8:
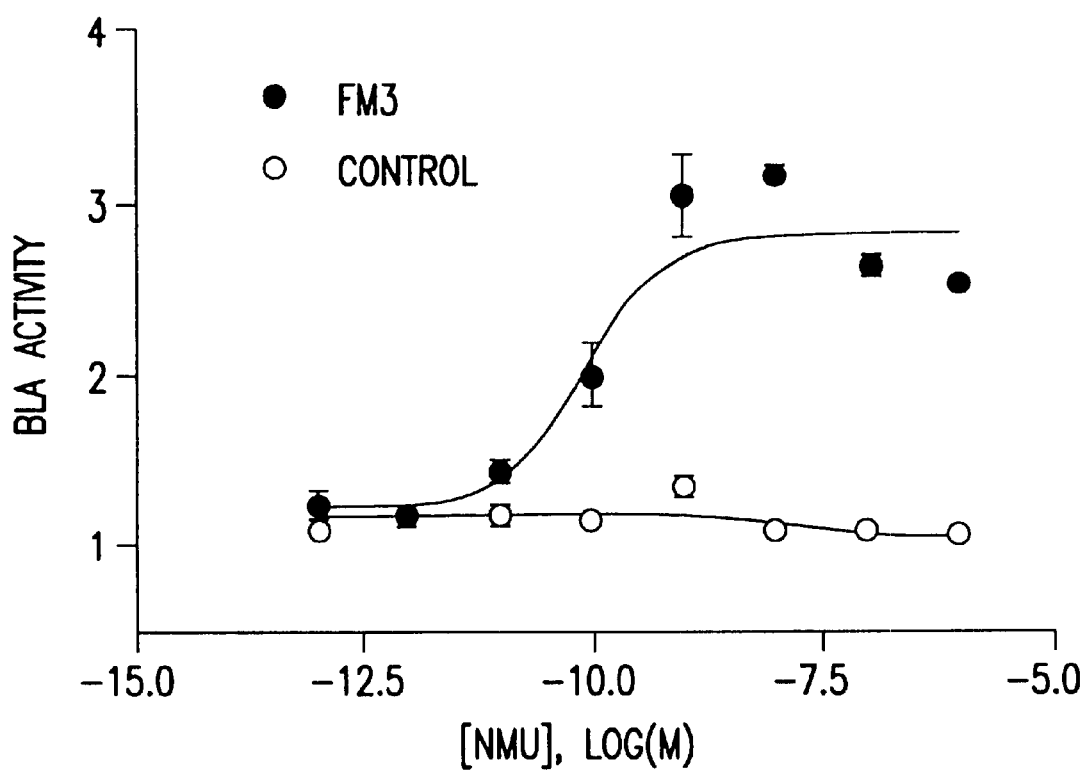

FIG. 8 illustrates the dose response of GHSR-R to NMU in CHO-NFAT-bla cells by β-lactamase assay. NMU was diluted by 10-fold serial dilutions and assayed in triplicates. The EC50 of NMU for GHSR-R in this assay is ~75 pM.

Figure 9:
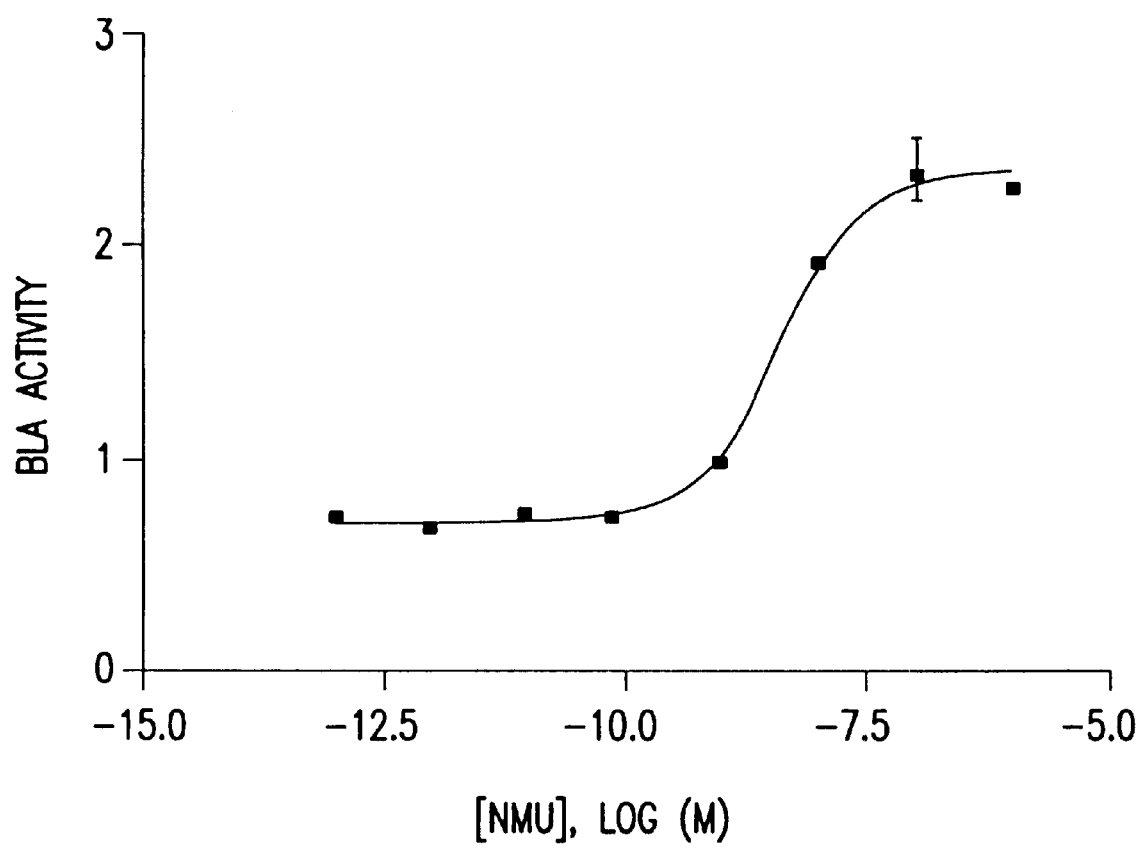

FIG. 9 illustrates the dose response of GHSR-R to NMU in HEK293CRE-bla cells by β-lactamase assay. NMU was diluted by 10-fold serial dilutions and assayed in triplicates. The EC50 of NMU for GHSR-R is about 3 nM in this assay.

Figure 10:
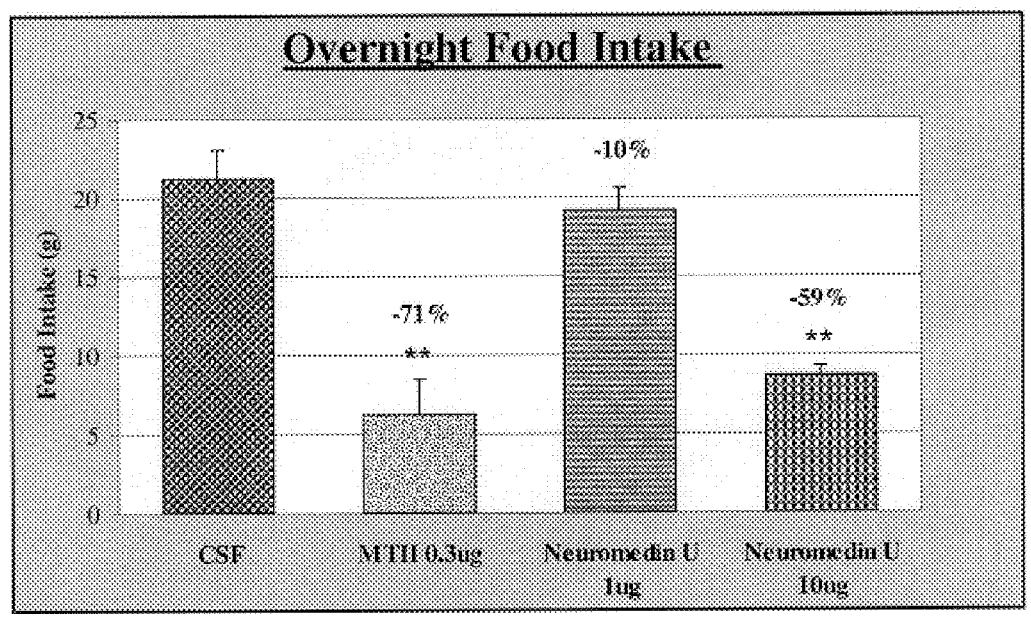

FIG. 10 illustrates the effect of NMU (1 and 10 μg) administered ICV (LV) on overnight food intake in lean CRL rats on ground (Purina #7012) rodent diet.

DETAILED DESCRIPTION OF THE INVENTION

As used throughout the specification and claims, the following definitions shall apply:

"Growth hormone secretagogue related receptor" or "GHSR-R" or "FM-3" includes an amino acid sequence encoded by a nucleic acid molecule or fragment thereof that (a) comprises the nucleotide sequence as set forth in SEQ ID NOs:1 or 3; (b) comprises a nucleic acid sequence encoding a polypeptide that is at least 70 percent identical, preferably at least 80 percent identical and most preferably at least 90 percent identical to the polypeptide encoded by SEQ ID NOs:2 or 4; (c) is a naturally occurring allelic variant of (a) or (b); (d) is a nucleic acid variant of (a)–(c); and/or (e) is complementary to (a)–(d). This term also includes peptide or polypeptide fragments derived from items (a)–(e) above, to the amino acid sequences set forth in SEQ ID NOs:2 or 4 and/or to chemically modified derivatives as well as nucleic acid and/or amino acid sequence variants thereof.

"GHSR-R derivative" or "GHSR-R variant" refers to a GHSR-R that has (1) been chemically modified, as for example, by addition of polyethylene glycol or other compound, and/or (2) contains one or more nucleic acid or amino acid sequence substitutions, deletions and/or insertions.

"Nucleic acid variant" refers to a sequence wherein one or more nucleotides have been designed to differ from the sequence at issue (in this case, GHSR-R).

"Stringent conditions" refers to such hybridization reaction parameters as the concentration and type of ionic species present in the hybridization solution, the types and concentrations of denaturing agents present, and the temperature of hybridization. These conditions are approximately 35° C. to 65° C. in a salt solution of approximately 0.015 to 0.9 molar NaCl. Generally as hybridization conditions become highly stringent (such as 0.1×SSC, 65° C.), longer probes are preferred if stable hybrids are to be formed. As a rule, the stringency of the conditions under which a hybridization is to take place will dictate certain characteristics of the preferred probes to be employed. Such relationships are well understood and can be readily manipulated by those skilled in the art.

"Binding domain" refers to that region or regions of the receptor which are able to bind to ligands.

"Ligand" refers to any molecule which binds to the GHSR-Rs of this invention. These ligands can have either agonist, partial agonist, partial antagonist or antagonist activity.

"Free from receptor-associated proteins" means the receptor protein is not in a mixture or solution with other membrane receptor proteins.

"Free from associated nucleic acids" means the nucleic acid is not covalently linked to DNA which it is naturally covalently linked in the organism's chromosome.

"Isolated receptor" means the protein is not in a mixture or solution with any other proteins.

"Isolated nucleic acid" means the nucleic acid is not in a mixture or solution with any other nucleic acid.

"Purified receptor" means the receptor is at least about 95% pure.

"Purified nucleic acid" means the nucleic acid is at least about 95% pure.

"Secretagogue-like compound" means any compound which exhibits substantially the same function as growth hormone secretagogues (i.e., stimulating growth hormone release).

"NMU" means neuromedin U.

"Ligand(s) sufficiently similar thereto" means any ligand which binds to the GHSR-R and causes some response.

A "GHSR-R agonist" is a compound which binds to GHSR-R and produces a cellular response which is at least about equivalent to that of neuromedin U and which may be greater.

A "GHSR-R antagonist" is a compound which binds to GHSR-R and produces a cellular response which is less pronounced than that of neuromedin U.

"Activation" means that the receptor is stimulated to carry out its normal function, herein indicated by release of the second messenger $Ca^{2+}$.

"Effective amount" means an amount effective in bringing about the intended result (i.e., decrease in food intake or treatment of obesity). Preferably, this dose is to be above 1 µg of neuromedin U or agonist thereof/kg body weight, more preferably, above 10 µg/kg, and most preferably, above 20 µg/kg.

The present invention relates to newly identified receptors, growth hormone secretagogue related receptors (GHSR-Rs), which exhibit moderate sequence identity to the growth hormone secretagogue receptor (GHS-R) and the neurotensin receptor (NT-R). More specifically, this invention relates to receptors comprising the sequence of SEQ ID NOs:2 or 4, the mouse and human receptor sequences, respectively. The human and murine GHSR-Rs exhibit strong protein sequence identity (73%). This invention also relates to proteins that are at least 90% homologous to said receptors. Receptors in accordance with this invention group as a separate branch distinct from both GHS-R and NT-R sequences and the orphan GPC-R's GPR38 and GPR39; see FIG. 2.

The receptors of this invention have been proven by Applicants to be high affinity receptors of neuromedin U (NMU), a neuropeptide widely distributed in the gut and central nervous system which causes potent contraction of rat uterine smooth muscle. The discovery of the first NMU receptor, designated GHSR-R, provides important information for understanding the biochemical mechanisms and physiological roles of NMU.

HEK293 cells and Cos-7 cells transfected with human GHSR-R showed strong, dose-dependent calcium mobilization in response to both the long form (rat NMU-23) and the short form (porcine NMU-8) of neuromedin U. Radioligand binding analysis showed high affinity binding of NMU (IC50=3 nM) to membrane preparations isolated from HEK293 cells stably expressing human GHSR-R. Further, CHO-NFAT-bla cells stably expressing GHSR-R showed a strong response to NMU when screened against NMU using the β-lactamase assay of Example 8. The following studies suggest GHSR-R most likely couples to the $Gq/G_{11}$ pathway since activation leads to strong calcium mobilization. Both rat NMU-23 and porcine NMU-8 were able to activate human GHSR-R with nanomolar affinity.

The mouse GHSR-R receptor sequence contains a single intron of approximately 3 kb at bp 878 (a perfectly conserved splice donor site: G/gt) interrupting the open reading frame sequence at amino acid $Asp^{293}$. This immediately follows the predicted TM domain 6 (exon 1: extracellular domain through TM-6; exon 2: third extracellular loop, TM-7 and C-terminal intracellular domain). Without being bound by theory, it is believed that a non-canonical leucine codon (Soldata et al. 1990 *J. Biol. Chem.* 265:4498–4506) serves as the initiator based on sequence similarity to the human sequence in this region and the absence of upstream in-frame methionine codons for an additional 308 basepairs.

By contrast, the human genomic sequence contains an initiator methionine codon in a favorable Kosak context (Kosak, M. 1984 *Nucleic acids res.* 12:857–872) with an in-frame stop codon present 102 bp upstream.

Both forms contain all the hallmark features of the 7-transmembrane domain (TM)-containing G-protein linked receptor superfamily (GPC-Ris or 7-TM receptors). These include the seven transmembrane regions, three intra- and extracellular loops, and the GPC-R protein signature sequence. Thus, GHSR-Rs, and specifically the sequences of SEQ ID Nos:2 and 4, constitute a new member of the GPC-R family of receptors. Not all regions are required for functioning, and therefore this invention also comprises functional receptors which lack one or more non-essential domains.

An expression profile derived from a Northern blot analysis revealed a predominate transcript size of approximately 5 kb, which was detected in all tissues examined. A band of approximately 2 kb was also noted in most of the tissues (with high abundance in testis), suggesting alternative mRNA processing of the GHSR-R primary transcript.

Southern blot analysis (FIG. 3B) of EcoRI-digested genomic DNA using the mouse form as a radiolabeled probe gave a simple hybridization pattern in all species tested, indicative of a single, highly conserved gene encoding GHSR-R.

It is to be noted that the GHSR-Rs and fragments thereof are immunogenic. Thus, another aspect of this invention is antibodies and antibody fragments which can bind to GHSR-R or a GHSR-R fragment. These antibodies may be monoclonal antibodies and produced using either hybridoma technology or recombinant methods. They may be used as part of assay systems or to deduce the function of a GHSR-R present on a cell membrane.

Another aspect of this invention are antisense oligonucleotides, nucleotides which can bind to GHSR-R nucleotides and modulate receptor function or expression.

Yet another aspect of this invention is a method of increasing the amount of GHSR-Rs on a cell membrane comprising, introducing into the cell a nucleic acid encoding a GHSR-R, and allowing expression of the GHSR-R.

A further aspect of this invention is a method of identifying ligands comprising contacting cells expressing GHSR-R with a compound suspected of being a ligand for said receptor and determining whether binding occurs, binding constituting a positive indication of the presence of a ligand. Ligands detected using the assays described herein may be used as modulators of endocrine function. Further, ligands capable of mimicking the functions of neuromedin U could be identified via this method.

Another aspect of this invention is a method of identifying ligands for GHSR-R which comprises contacting cells expressing the GHSR-R receptor with a compound suspected of being a ligand specific for said receptor in the presence of jelly fish aequorin or other suitable reporter responsive to $Ca^{2+}$ mobilization, and monitoring for luminescence or other signal from the reporter indicating activation of the receptor, activation constituting a positive indication of the presence of a ligand. The aequorin assay is a sensitive method to measure $Ca^{2+}$ mobilization based on bioluminoscence of jelly fish aequorin in the presence of $Ca^{2+}$; Button and Brownstein, 1993 *Cell Calcium* 14:663–671. Other suitable assay systems responsive to $Ca^{2+}$ mobilization include the use of various fluorescent dyes that monitor $Ca^{2+}$ concentration change (Kao et al., 1989, *J. Biol. Chem.*, 264:8179–8184), and the use of transcription-based reporter systems that monitor changes of calcineurin activity (Zlokarnik et al., 1998, *Science,* 279:84–88).

Another aspect of the instant invention is a method of identifying ligands for GHSR-R which comprises contacting cells expressing the GHSR-R receptor with a compound suspected of being a ligand specific for said receptor, and monitoring for changes in concentration of intracellular cyclic AMP (cAMP); an increase in cAMP constituting a positive indication of the presence of a ligand. Suitable assay systems capable of monitoring cAMP changes include direct measurement of intracellular concentrations of cAMP by ELISA and the use of transcription-based reporter assays that are responsive to cAMP changes.

An additional aspect of the invention is a method for determining whether a substance is a potential agonist or antagonist of GHSR-R comprising contacting cells expressing the GHSR-R receptor with labeled neuromedin U in the presence and in the absence of the substance, and measuring the binding of neuromedin U to GHSR-R, where if the amount of binding of neuromedin U is more or less in the presence of the substance than in the absence of the substance, then the substance is a potential agonist or antagonist of GHSR-R, respectively. Agonists are useful in the treatment, control, or prevention of diseases, disorders or conditions responsive to the activation of the neuromedin U receptor. As such, agonists could be useful in the treatment, control or prevention of depression, anxiety, compulsion, neuroses, insomnia/sleep disorders, substance abuse, pain, neuroprotective and cognitive disorders, and memory enhancement including the treatment of Alzheimer's disease.

A further aspect of the instant invention is a method of determining whether a substance is a potential agonist of GHSR-R which comprises contacting cells expressing the GHSR-R receptor with the substance in the presence of jelly fish aequorin or other suitable reporter responsive to $Ca^{2+}$, and monitoring for luminescence or other signal from the reporter indicating activation of the receptor; activation constituting a positive indication of the presence of an agonist. The aequorin assay is a sensitive method to measure $Ca^{2+}$ mobilization based on bioluminescence of jelly fish aequorin in the presence of $Ca^{2+}$; Button and Brownstein, 1993 Cell Calcium 14:663–671. Other suitable assay systems responsive to $Ca^{2+}$ mobilization include the use of various fluorescent dyes that monitor $Ca^{2+}$ concentration change (Kao et al., 1989, J. Biol. Chem., 264:8179–8184), and the use of transcription-based reporter systems that monitors changes of calcineurin activity (Zlokarnik et al., 1998, Science, 279:84–88).

Another aspect of the instant invention is a method of determining whether a substance is a potential antagonist of GHSR-R which comprises contacting cells expressing the GHSR-R receptor first with the substance and then with neuromedin U in the presence of jelly fish aequorin or other suitable reporter responsive to $Ca^{2+}$, and monitoring for luminescence or other signal from the reporter indicating activation of the receptor; where if the amount of luminescence or signal is less in the presence of the substance than in the absence of the substance, then the substance is a potential antagonist of GHSR-R.

Another aspect of the instant invention is a method of determining whether a substance is a potential agonist of GHSR-R which comprises contacting cells expressing the GHSR-R receptor with the substance, and monitoring for changes in cyclic AMP (cAMP); an increase in cAMP constituting a positive indication of an agonist. Assay systems capable of monitoring cAMP changes include direct measurement of intracellular concentrations of cAMP by ELISA, and the use of transcription-based reporter assays that are responsive to cAMP changes.

Another aspect of the instant invention is a method of determining whether a substance is a potential antagonist of GHSR-R which comprises contacting cells expressing the GHSR-R receptor with the substance, and monitoring for changes in cyclic AMP (cAMP); a marginal (non-biologically significant) to no increase in cAMP constituting a positive indication of an antagonist.

A further aspect of the instant invention is a method of decreasing food intake of a mammal which comprises administering to said mammal an effective amount of neuromedin U or a GHSR-R agonist. Applicants were the first to identify that neuromedin U could be used in the regulation of food intake. Upon administration of neuromedin U to rats, there was a suppression of food intake. Accordingly, selectively modulating GHSR-R receptor signaling may be an approach to treatment of human obesity and other eating disorders. Obesity, a condition defined as being 20% over one's ideal body weight, is a serious public health concern in the industrialized world. According to the National Institutes of Health, over 97 million Americans are overweight or obese. Obesity predisposes individuals to potentially life-threatening conditions such as hypertension, stroke, heart disease and diabetes and is the second leading cause of preventable deaths in the US. Identification of weight-regulating therapeutics (agonists) that modulate the GHSR-R receptor may lead to new drugs for the treatment of obesity and other weight disorders. Agonists found with this invention would be useful in the treatment, control or prevention of obesity (by reducing appetite, increasing metabolic rate, reducing fat intake and/or reducing carbohydrate craving) and other disorders affected by the intake of food.

Moreover, cachexia (malnutrition) is estimated to be responsible for approximately 40% of all cancer deaths. Accordingly, therapeutics inducing weight gain, such as antagonists of the GHSR-R gene could serve an important area of medical need. In this respect, a method included within the instant invention would be a method of increasing food intake of a mammal which comprises administering to said mammal an effective amount of a GHSR-R antagonist.

Another aspect of the instant invention is a method for the treatment or prevention of obesity which comprises administering to a mammal in need of such treatment or prevention an effective amount of neuromedin U or a GHSR-R agonist.

Yet one further aspect of the present invention is a method by which to determine whether a compound of interest binds to both GHSR-R and GHS-R. This is useful for identifying compounds with very specific binding characteristics (e.g., those that only bind one receptor as opposed to the other) which would be helpful when a very specific ligand is needed as well as for identifying those compounds which perhaps have a complementary or, adversely, an antagonistic effect in binding both receptors.

The following, non-limiting Examples are presented to better illustrate the invention.

EXAMPLE 1

Isolation of the Mouse GHSR-R

A mouse EST (dEST database assession # AA562357, deposited Aug. 18, 1997) derived from a T-cell library was identified with a significant homology score (P (N) 1.3× 10–12) to the human GHS-R TM domains 6–7 (residues 265–366). Upon further analysis, EST 562357 exhibited good sequence identity (63% DNA, 36 % amino acid) to the 3' end of the gene for the human GHS-R. A murine T cell 1XR cDNA library (Stratagene) was screened with the mouse EST 562357 probe (455 bp in length) under high-stringency conditions. Four partial clones were identified after three rounds of screening. Additional clones were isolated from mouse thymus poly $(A)^+$ RNA via 5' Race Marathon cDNA Amplification (Clontech). PCR of the 1XR cDNA library with gene specific primers and the library adaptor primer resulted in the isolation of a full-length clone. Screening of a 1FixII mouse genomic library (Stratagene)

identified eight positive clones to aid in the determination of the correct start codon.

EXAMPLE 2
Isolation of the Human GHSR-R

To isolate the human isoform, a human PAC library (Genome Systems) was hybridized (32° C. in 50% formamide, 5×SSPE) and washed at moderate stringency (55° C., 1×SSC) with a probe derived from the ORF of the mouse isoform. Two positive clones were identified. The PAC clones were isolated and subjected to restriction enzyme digestion and Southern blotting providing a BamH1 fragment of approximately 5 kb containing the complete ORF for the human isoform. DNA was sequenced on both strands using dye terminator cycle sequencing ready reactions (Perkin Elmer-ABI), and analyzed on a 377 ABI Prism cycle sequencer.

EXAMPLE 3
Comparison of GHSR-R to Other Members of the GHS-R/NT-R Family

Protein sequences were aligned using the Pileup program (Wisconsin Package Version 9.1, Genetics Computer Group (GCG), Madison, Wis.; gap extension 4, gap creation 12); results indicated in FIG. 2. Identical residues are boxed. The sequences used in the alignment and their Genbank database assession numbers are: human GHS-R (HSU60179); human NT-R type 1 (X70070); human NT-R type 2 (2494989); human GPR38 (AF034632); human GPR39 (AF034633).

EXAMPLE 4
Expression Profile via Northern Blot Analysis

A commercial RNA blot (Clontech) containing poly (A)$^+$ mRNA (1 µg/lane) from several mouse tissues was hybridized with a radiolabeled probe encompassing the mouse GHSR-R ORF. Following high-stringency post-hybridizational washing, the blot was exposed to X-ray film for four days at −70° C. RNA size marker (Life Technologies) are, in kb, 9.5, 7.5, 4.4, 2.4, and 1.35.

The predominate transcript size was approximately 5 kb, which was detected in all tissues examined. A band of approximately 2 kb was also noted in most of the tissues (with high abundance in testis), suggesting alternative mRNA processing of the GHSR-R primary transcript.

EXAMPLE 5
Expression Profile via Southern Blot Analysis

A genomic Southern blot (EcoRI-digested DNA, 10 mg/lane) was hybridized with a 3' fragment of the human GHSR-R ORF (third intracellular loop to C-terminal intracellular domain). Post-hybridizational washing stringencies were at 55° C., 4×SSPE after which the filters were dried and exposed to X-ray film for 5 days at −70° C. Lambda Hind III DNA markers were (in kb), 23.1, 9.4, 6.6, 4.4, 2.3, 2.1.

Using the mouse form as a radiolabeled probe, the results revealed a simple hybridization pattern in all species tested, indicative of a single, highly conserved gene encoding GHSR-R.

EXAMPLE 6
Construction of GHSR-R-Expressing Plasmid

The complete coding sequence of human GHSR-R was amplified by PCR using plasmid containing human GHSR-R as template with two primers, the forward primer, FM3EcoRV.F, 5'-CTGAGATATCACCACCATGGCTTGCAATG-GCAGTGC-3' and the reverse primer, hFM3BamHI.R, 5'-AGTCGGATCCGTATC-AGGATGGATCGGTCTCTTGCT. The forward primer contained an EcoRV site and consensus Kozak (ACCACC) sequence for translation immediately upstream of the initiation codon. The reverse primer contained an BAMHI site downstream of the stop codon.

PCR reactions were carried out using the DNA polymerase PFU turbo (Stratagene, La Jolla, Calif., USA) following the conditions of the enzyme supplier. The PCR product was purified, digested by EcoRV plus BamHI, and ligated into the vector pIRESpuromycin (Clontech, Palo Alto, Calif., USA) which was also digested with EcoRV and BamHI-using T4 DNA ligase. The ligation product was transformed into *E.coli*. Clones containing the correct construct were identified by restriction digestion and verified by DNA sequencing. The resulting plasmid is called GHSR-R-pIRESpuro.

EXAMPLE 7
Generation of GHSR-R-expressing Cells

Plasmid DNA of GHSR-R-pIRESpuro was linearized by digestion with Fspl and transfected into CHO-NFAT-bla cells and HEK293CRE-bla cells (Aurora Biosciences, San Diego, Calif., USA), and HEK293aequorin cells using lipofectamine (GIBCO-BRL, Gaithersburg, Md., USA) by following the conditions suggested by GIBCO-BRL. Three days after transfection, the cells were detached by trypsin digestion, diluted by 1:5 in complete culture medium plus puromycin at 5.0 µg/ml for CHO-NFAT-bla cells, or 0.5 µg/ml for both HEK293CRE-bla cells and HEK293aequorin cells. Cells were incubated at 37° C./5% $CO_2$ and replaced with fresh medium twice per week. Two weeks after transfection, puromycin-resistant cells were detached by trypsin digestion, combined, and propagated for screening.

EXAMPLE 8
Aequorin Bioluminescence and β-lactamase Assays

Aequroin bioluminescence assays were carried out following the protocol of Button and Brownstein (1993 *Cell Calcium* 14:663–71) with minor modification. ECB (extracellular buffer) was replaced by Ham's F12 medium (with 0.3 mM $CaCl_2$, 0.1% fetal bovine serum, 25 mM HEPES, pH7.3).

HEK293aeq/17 cells stably expressing GHSR-R were maintained at 37° C./5% $CO_2$ in DMEM+10% fetal bovine serum (heat inactivated), 1 mM sodium pyruvate, 500 µg/ml neomycin G418, 0.5 µg/ml puromycin (GIBCO-BRL, Gaithersburg, Md., USA). Cells were seeded by 1:4 dilution in T75 flasks two days before assay. The day the assay was performed, cells at 80–90% confluency were washed twice with DMEM+0.1% fetal bovine serum, and then charged for one hour at 37° C./5% $CO_2$ in DMEM containing 8 µM coelenterazine cp (Molecular Probes, Eugene, Oreg., USA) and 30 uM glutathione. Cells were then washed once with versene (GIBCO-BRL, Gaithersburg, Md., USA), detached using Enzyme-free dissociation buffer (GIBCO-BRL, Gaithersburg, Md., USA) and resuspended in Ham's F12 medium (with 0.3 mM $CaCl_2$, 0.1% fetal bovine serum, 25 mM HEPES, pH7.3). The cell suspension was centrifuged at 300 g for 5 min. The supernatant was removed, and the pellet was then resuspended in 10 mL ECB. The cell density was determined by counting with a hemacytometer and adjusted to 500,000 cells/ml in ECB.

Neuromedin U was diluted in ECB (as modified above) using 5-fold serial dilutions, and aliquoted into assay plates in triplicates at 0.1 ml/well. The cell suspension was injected at 0.1 ml/well, read and integrated for a total of 20 seconds using Dynex MLX luminometer (Dynex Technologies, Middlesex, UK). Data were analyzed using the software GraphPad Prism Version 3.0 (GraphPad Software, Inc., San Diego, Calif., USA).

Figure 4A:
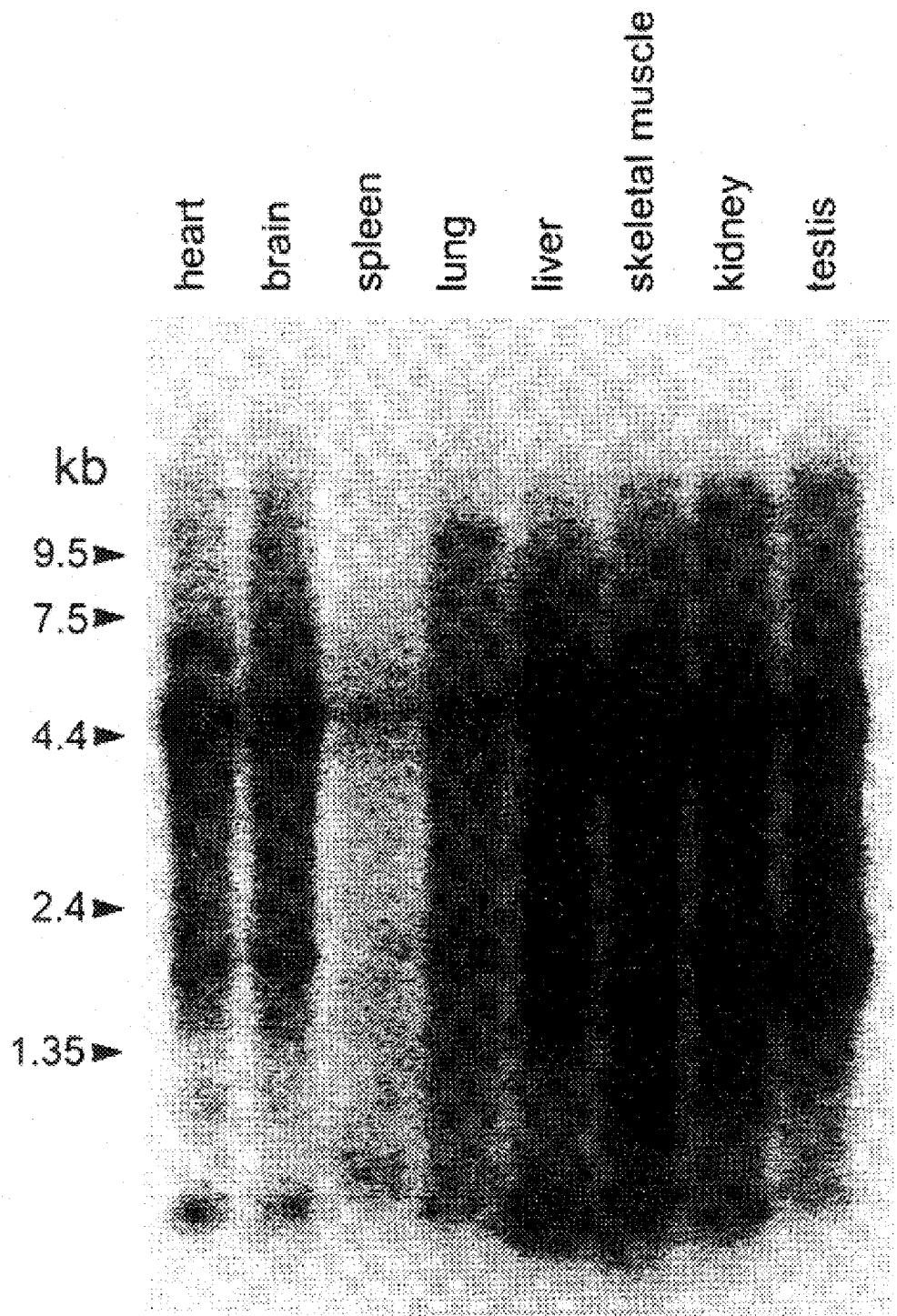
FIG. 4A is a Northern Blot Analysis of GHSR-R expression.
Figure 4B:
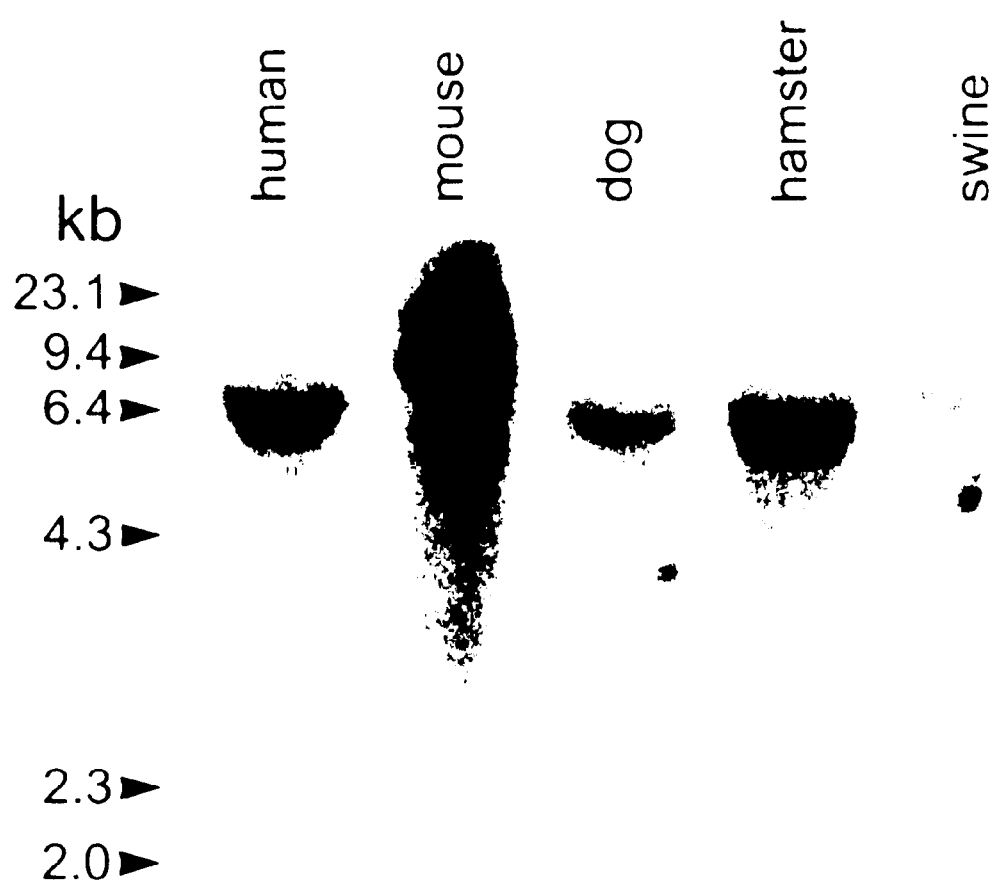
FIG. 4B is a Southern Blot Analysis of GHSR-R expression.
Figure 5:
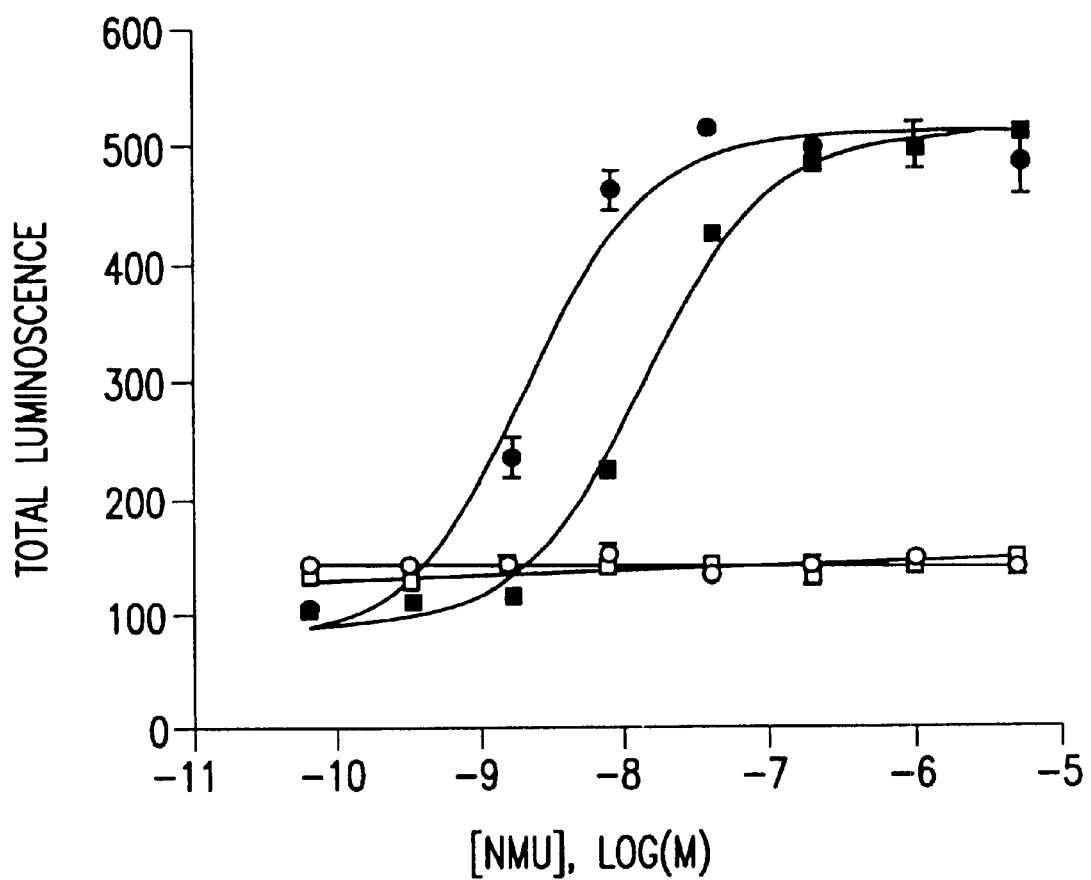
FIG. 5 illustrates activation of GHSR-R by NMU by the aequorin assay. HEK293/aeq cells stably expressing GHSR-R (solid symbols) and untransfected cells (open symbols) were assayed (n=3) against 5-fold serial dilutions of rat NMU-23 (circles) and porcine NMU-8 (squares).

GHSR-R-expressing cells showed a strong, dose-dependent response to both rat NMU-23 and porcine NMU-8 (FIG. 5). The EC50 of rat NMU-23 and porcine NMU-8 in these cells is 14.1 nM and 2.1 nM, respectively, suggesting both peptides are likely endogenous ligands of GHSR-R. Untransfected cells showed no response to either form of NMU at the highest concentration tested (FIG. 5). Cells transfected with plasmids expressing other G-protein coupled receptors cloned into the same vector did not show any response to NMU either. The results indicate that both porcine and rat NMU can activate GHSR-R with high affinity and lead to $Ca^{2+}$ mobilization, most likely through the $G\alpha q/G_{11}$ pathway.

β-lactamase assays were carried out as described previously; Zlokarnik et al., 1998, *Science* 279:84–88. CH.3xNFAT-bla cells (Aurora Biosciences, San Diego, Calif., USA) stably expressing GHSR-R were maintained at 37° C./5% $CO_2$ in DMEM+10% fetal bovine serum (GIBCO-BRL, Gaithersburg, Md., USA), 1 mM sodium pyruvate, 1 mM non-essential amino acid, 55 μM 2-mecaptoethanol, 250 μg/ml zeocin, 5.0 μg/ml puromycin. Cells were seeded at 7,000 cells/well in 96-well clear bottom black-walled plates two days before assay.

The day the assay was performed, growth media was removed from the cells and replaced with 0.05 mL/well of phenol red-free Opti-MEM (GIBCO-BRL, Gaithersburg, Md., USA). Neuromedin U was diluted in Opti-MEM using 5-fold serial dilutions, and added into assay plates in triplicates at 0.05 ml/well. The plates were incubated at 37° C./5% $CO_2$ for 4 hours.

CCF2AM (Aurora Biosciences, San Diego, Calif., USA) dye was prepared as follows: To 60 μl of Solution B (100 mg/ml of Pluroic-F127 in DMSO containing 0. 1% acetic acid), 12 μl of Solution A (1 mM of CCF2AM in dry DMSO) was added. The mixture was mixed well and then added with vigorous agitation to 925 μl Solution C (24% w/w PEG-400, 12 ESS (Aurora Biosciences, San Diego, Calif., USA) w/v). 75 μL of Solution D (200 mM prbenecid dissolved in 200 mM NaOH) was added and then mixed. The resulting dye mixture was loaded at 20 μl/well onto the cells. The cells were then incubated at room temperature for one hour.

Fluorescence was measured at emission wave length of 460 nM and 535 nM using an excitation wave length of 405 nM in a Tecan SpectraFluor Plus fluorescence microplate reader (Tecan Austria, Saltzburg, Austria). The ratio of fluorescence between 460 nM and 535 nM was calculated and plotted using the software GraphPad Prism Version 3.0 (GraphPad Software, Inc., San Diego, Calif., USA).

CHO-NFAT-bla cells stably expressing GHSR-R showed a strong response to NMU when screened against NMU using the β-lactamase assay. The dose response of GHSR-R in CHO-NFAT-bla cells is shown in FIG. 8. HEK293CRE-bla cells stably expressing GHSR-R were also screened against NMU using the β-lactamase assay and, too, showed a strong response to NMU. The dose response of GHSR-R in HEK293CRE-bla cells is shown in FIG. 9.

EXAMPLE 9

FLIPR Assay

COS-7 cells were transiently transfected with GHSR-R-pIRESpuromycin and control vector using lipofectamine (GIBCO-BRL). Two days after transfection, cells were detached with enzyme-free dissociation buffer and seeded into 96-well plates at 15,000 cells/well. After 24 h, cells were loaded with Calcium Green-1 in the presence of 2.5 mM probenicid. After washing, the cells were treated with varying concentrations of NMU. Fluorescence output was measured by a Fluorometric Imaging Plate Reader (FLIPR, Molecular Devices, Inc.).

Figure 6:
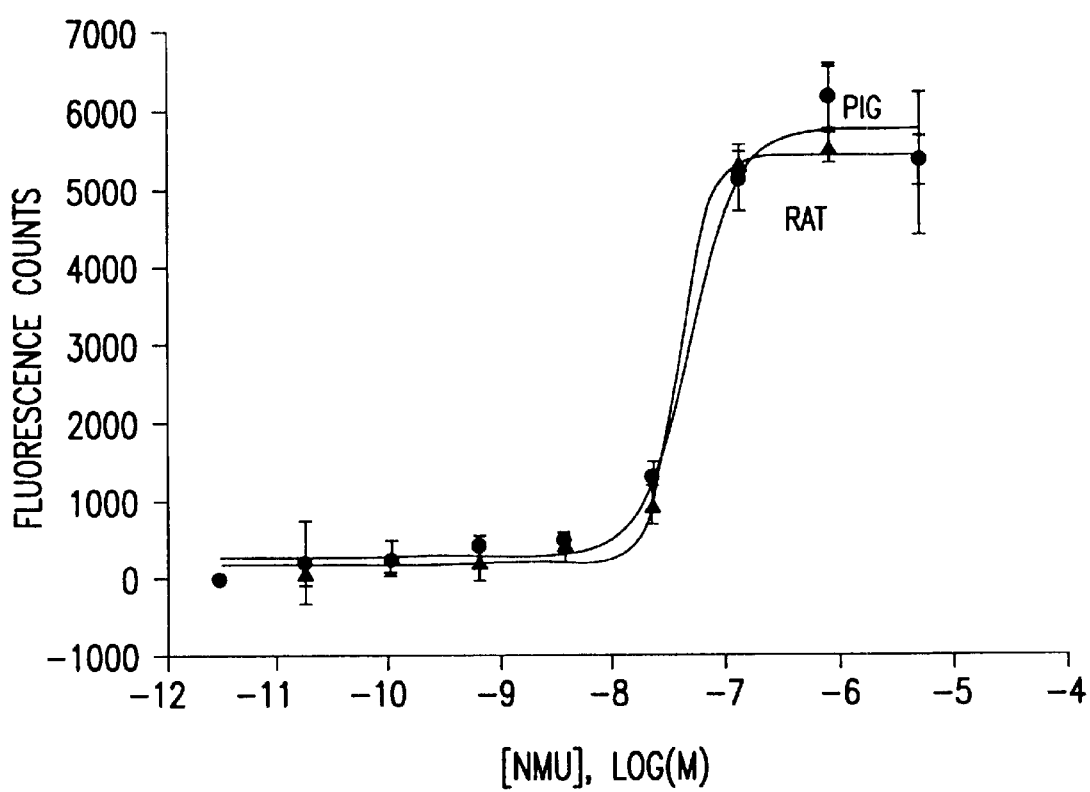
FIG. 6 illustrates activation of GHSR-R by NMU assayed with FLIPR (Fluorometric Imaging Plate Reader, Molecular Devices, Inc.). Cos-7 cells were transiently transfected with GHSR-R/pIRESpuromycin and control vector and assayed versus rat NMU-23 (triangles) and porcine NMU-8 (circles) 72 hours later (n=6).

FLIPR monitors changes of intracellular $Ca^{2+}$ concentration in real time. As shown in FIG. 6, cells transfected with GHSR-R/pIRESpuromycin showed a dose-dependent response to both rat and porcine NMU. The EC50 of rat NMU-23 and porcine NMU-8 was 55 nM and 45 nM, respectively, confirming that NMU is able to activate GHSR-R and cause $Ca^{2+}$ mobilization.

EXAMPLE 10

Radio-ligand Binding Assay

Cell membrane preparation: HEK-293/aeq17cells stably expressing human GHSR-R (3 T-175 tissue culture flasks, ~30×10⁶ cells) were harvested by scraping, washed once in 50 mM Tris-HCl, pH 7.4, 5 mM MgCl2, and centrifuged at 2000×g for 15 minutes. All procedures were conducted on ice. Cell pellets were homogenized in a tissue grinder with a PTFE pestle (25 strokes). Crude cell membranes were then isolated by centrifugation of the cell lysate at 13,000×g for 30 minutes. Membrane pellets were resuspended at a protein concentration of 2.8 mg/ml in 50 mM Tris-HCl, pH 7.4, 5 mM MgCl2.

Figure 7:
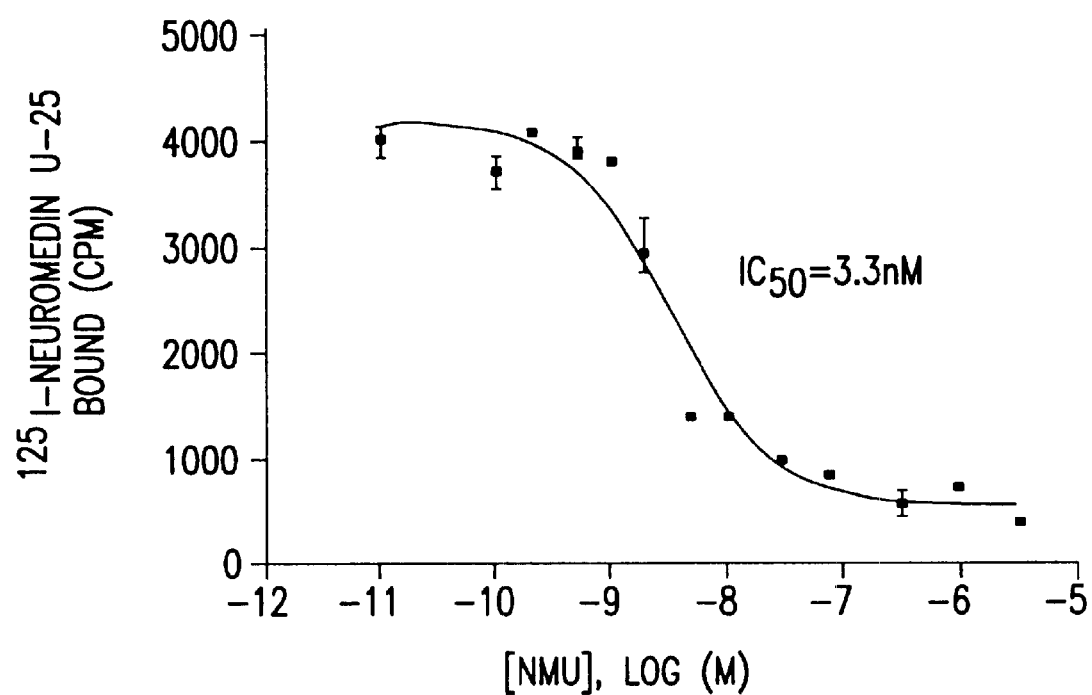
FIG. 7 is a radioligand binding assay of NMU. Competition for 125I-labeled rat NMU-23 was performed using HEK293/aeq cells stably expressing GHSR-R.

Binding of rat $^{125}$I-neuromedin U-25 to Cell Membranes Expressing human GHSR-R: Neuromedin U-25 (rat) was labeled with $^{125}$I at its N-terminal tyrosine residue (Woods Assay, Portland, Oreg.) to a specific activity of 2000 Ci/mmol. The binding solution (0.5 ml in 12×75 mm borosilicate glass tubes) contained 4 μg GHSR-R expressing cell membrane, 0.1 nM $^{125}$I-neuromedin U-25 in 25 mM Tris-HCl, pH 7.4 buffer with 2 mM EDTA, 10 nM MgCl2 and 100 μg/ml bacitracin. After incubation for 1 hour at room temperature, binding reactions were filtered through GC/C filters (Whatman; presoaked for 1 hour in 1% polyethylenimine) on a 48-well cell harvester (Brandel), washed 3×3 ml with ice-cold 50 mM Tris-HCl, pH 7.4 buffer with 10 mM MgCl2. Radioactivity on the filters was quantitated by gamma counting. Competition analysis for the binding of $^{125}$I-neuromedin U-25 to GHSR-R expressing cell membranes indicates the presence of a high affinity binding site with a $IC_{50}$ of 3.3 nM for unlabeled rat neuromedin U-25. As shown in FIG. 7, rat NMU-23 displayed an IC50 of 3.3 nM under the conditions tested.

EXAMPLE 11

Decreasing Food Intake with Neuromedin U

Animals and Diet: Male rats (Charles River Sprague Dawley) weighing 250–350 g were maintained in a temperature and humidity controlled facility with a 12 hour light/dark cycle (4:00 AM lights on). Rats were fed standard rodent ground chow (Purina#7012). Fresh diet was provided daily. Both food and water were supplied ad libitum throughout both the pre- and post-surgery periods.

ICV cannulation: Rats under ketamine/xylazine anesthesia, were stereotaxically implanted in the lateral ventricle with a 26G guide cannula. The guide cannula (Plastics One Roanoke,Va.) was secured with three set screws and dental cement. A dummy internal cannula was placed into the guide cannula to maintain cannula patency. Rats were individually housed in Nalgene metabolism cages and allowed to recover a minimum of seven days before injection with test compounds.

Acclimation: Beginning the day after surgery, each rat was acclimated to the handling and injection procedure, as well as, the feeding regimen. At approximately 10:00 AM, all rats were presented with fresh chow diet. They were allowed free access to the fresh diet for one hour in order to induce satiation. At the end of the satiation period food was weighed and each rat was handled using minimal restraint and its dummy cannula was removed. Removing the dummy cannula daily ensured cannula patency and acclimated the animal to the injection procedure. The rat was then returned to its cage. Food intake was measured two hours later and the following morning. Daily handling familiarized the rats with the injection procedure and minimized associated stress, an important consideration in feeding behavior studies where stress can cause hormonal changes in the body that can effect food intake. Rats were not used in any experimental protocols until their food intake returned to normal.

Lateral ventricle injections: All test substances were dissolved in artificial cerebral spinal fluid (aCSF; Harvard Apparatus, Holliston Mass.). Injections were in a volume of 400 nl. An injector was constructed consisting of a 10 μl Hamilton syringe (Hamilton Co. Reno, Nev. Model No. 701) with a 33 G needle. The length of the needle was such that it would extend 1 mm below the tip of the guide cannula when inserted. The syringe was attached to a Hamilton repeater. The injector was calibrated so that two pulses of the repeater delivered 400 nl of solution. The needle was held in place for approximately 30 seconds and was then removed very slowly to prevent backflow of the injected material.

Confirmation of cannula placement: Once the rats were fully recovered from surgery, guide cannula placement was confirmed by evaluating the food intake induced by the injection of 5 μg of hNPY (Peninsula Laboratories, Belmont, Calif.) after a one hour satiation period. Two hour post-injection food intake was recorded for each rat. The guide cannula was considered to be in the correct location if the NPY-induced two hour food intake was at least twice that of the two hour food intake recorded on the previous non-injection day. Rats were allowed a minimum of 72 hours between NPY injection and any test compound injection. Only NPY responsive rats were used in the experimental protocol. Cannula patency was reconfirmed after each test injection.

Test Compounds: NPY responsive rats were first injected ICV with aCSF to determine basal overnight food intake. To assess the possible role of the GHSR-R receptor in controlling spontaneous food intake, rats (n=6) were injected ICV with 1 or 10 μg of the ligand peptide NMU (rat, Phoenix Pharmaceuticals, Mountainview, Calif.). Additional rats were injected ICV with 0.3 μg of the peptide melanocortin agonist MTII (Peninsula Laboratories, Belmont, Calif.) as a positive control; see Murphy et al., 1998 *Neuropeptides* 32:491–497.

Data analysis: Food intake measurements were taken on individual rats at different times and under different treatment regimens using a cross-over study design. In this paradigm, each rat received a vehicle dose, as well as, one or more test doses. Food consumption of treated rats was compared to aCSF vehicle treated rats using an unpaired two-tailed t-test. Percent changes in food intake were calculated relative to the aCSF vehicle from each animal. Group comparisons were made using an unpaired two-tailed t-test.

Results: The 10 μg dose of NMU produced a 59% (P<0.01) suppression of food intake; see FIG. 10.

What is claimed:

1. An isolated nucleic acid encoding a receptor of the amino acid sequence set forth in SEQ ID NO: 4.

2. A vector comprising the nucleic acid of claim 1.

3. An isolated host cell comprising the vector of claim 2.

4. An isolated nucleic acid comprising the nucleotide sequence of SEQ ID NO: 3.

5. A vector comprising the nucleic acid of claim 4.

6. An isolated host cell comprising the vector of claim 5.

* * * * *